(12) United States Patent
Lewis et al.

(10) Patent No.: US 12,427,555 B2
(45) Date of Patent: Sep. 30, 2025

(54) LATERAL COLLECTION GRID FOR LANDFILL GAS AND METHOD

(71) Applicant: Watershed Geosynthetics, LLC, Alpharetta, GA (US)

(72) Inventors: Delaney Lewis, Downsville, LA (US); Jose Urrutia, Suwanee, GA (US)

(73) Assignee: Watershed Geosynthetics LLC, Alpharetta, GA (US)

( * ) Notice: Subject to any disclaimer, the term of this patent is extended or adjusted under 35 U.S.C. 154(b) by 109 days.

(21) Appl. No.: 18/221,862

(22) Filed: Jul. 13, 2023

(65) Prior Publication Data
US 2024/0017308 A1     Jan. 18, 2024

Related U.S. Application Data

(60) Provisional application No. 63/389,344, filed on Jul. 14, 2022.

(51) Int. Cl.
    *B09B 5/00*       (2006.01)
    *B09B 1/00*       (2006.01)

(52) U.S. Cl.
    CPC .................... *B09B 1/006* (2013.01)

(58) Field of Classification Search
    CPC ................. B09B 1/004; B09B 1/006
    See application file for complete search history.

(56) References Cited

U.S. PATENT DOCUMENTS

| | | |
|---|---|---|
| 994,155 A | 6/1911 | Harris |
| 3,563,038 A | 2/1971 | Healy et al. |
| 4,057,500 A | 11/1977 | Wager |

(Continued)

FOREIGN PATENT DOCUMENTS

| | | |
|---|---|---|
| CA | 2154239 | 1/1997 |
| CN | 112063498 | 12/2020 |

(Continued)

OTHER PUBLICATIONS

International Search Report and Written Opinion of the International Searching Authority for PCT Application No. PCT/US2018/061094, dated Feb. 20, 2019~1523.

(Continued)

*Primary Examiner* — Benjamin F Fiorello
(74) *Attorney, Agent, or Firm* — GARDNER THORPE

(57) ABSTRACT

A gas collection grid for use at landfills having a gas-producing waste pile, including a lower geocomposite positioned over the gas-producing waste pile, a protective layer of soil is positioned over the lower geocomposite. An upper geocomposite is positioned over the protective layer of soil such that the protective layer of soil is positioned between the lower and upper geocomposites. An impermeable geomembrane is positioned over the upper geocomposite. A cruciform gas collector conduit grid is positioned within or atop the protective layer of soil and has a plurality of collection orifices formed adjacent the vertical openings formed in the protective layer of soil. The impermeable geomembrane is non-perforated adjacent the collection orifices and the cruciform gas collector conduit grid is adapted for delivering collected gas laterally from beneath the geomembrane rather than vertically through the geomembrane.

8 Claims, 24 Drawing Sheets

(56) References Cited

U.S. PATENT DOCUMENTS

| | | | |
|---|---|---|---|
| 4,317,452 A | 3/1982 | Russo et al. | |
| 4,442,901 A | 4/1984 | Zison | |
| 4,596,491 A | 6/1986 | Dietzler | |
| 4,670,148 A * | 6/1987 | Schneider | B09B 1/00 210/603 |
| 5,857,807 A * | 1/1999 | Longo, Sr. | E21B 43/305 405/129.95 |
| 6,280,117 B1 | 8/2001 | Obermeyer et al. | |
| 8,292,543 B2 * | 10/2012 | Hater | B09B 3/00 405/129.95 |
| 8,313,921 B2 * | 11/2012 | Kraemer | C12M 23/18 405/129.95 |
| 8,777,515 B1 | 7/2014 | Donlin | |
| 8,926,221 B2 * | 1/2015 | Hwang | B09C 1/00 405/129.57 |
| 10,697,145 B2 | 6/2020 | Lewis | |
| 11,633,767 B2 * | 4/2023 | Shana'a | B09B 1/004 405/129.2 |
| 2004/0062610 A1 | 4/2004 | Hater et al. | |
| 2005/0201831 A1 * | 9/2005 | Lee | B09B 3/00 405/129.95 |
| 2005/0269253 A1 | 12/2005 | Potts | |
| 2006/0034664 A1 | 2/2006 | Augenstein et al. | |
| 2011/0045580 A1 * | 2/2011 | Hater | C12M 23/18 435/290.4 |

FOREIGN PATENT DOCUMENTS

| | | |
|---|---|---|
| DE | 19703826 | 8/1998 |
| EP | 0075993 | 4/1983 |
| RU | 2730310 | 8/2020 |

OTHER PUBLICATIONS

European Search Report, Application No. EP23185685, dated Dec. 21, 2023, 6 pages.

Abedi Mohammadmahdi et al., "Smart Geosynthetics and Prospects for Civil Infrastructure Monitoring: A Comprehensive and Critical Review", Institute for Sustainability and Innovation in Structural Engineering, School of Engineering, University of Minho, Campus De Azurem, 4800-058 Guimaraes, Portugal, vol. 15, No. 12, Jun. 8, 2023 (Jun. 8, 2023), p. 9258, XP093102017, DOI: 10.3390/sul5129258.

European Search Report, Application No. EP23185691, dated Jan. 2, 2024, 5 pages.

International Search Report & Written Opinion of the International Searching Authority, Application No. PCT/US2023/027709, dated Oct. 13, 2023, 9 pages.

International Search Report & Written Opinion of the International Searching Authority, Application No. PCT/US2021/016825, dated Mar. 2, 2021, 10 pages.

* cited by examiner

LATERAL COLLECTION GRID FOR LANDFILL GAS AND METHOD

BACKGROUND

In many instances, a fluid needs to be moved over a large distance or collected over a large area. For example, as waste material decomposes in a landfill, it gives off various gases. In the past, it has been known to use pumps, piping, and wellheads to extract the gases from the landfill and collect the same. Such wellheads are often spaced about one per acre in a grid pattern. Such systems of collecting the gases can be shut down by many factors, including power failures. To prevent the undesirable build-up of such gases in the event of non-operation of the extraction system, it has often been known to employ a grid pattern of vents spaced between the extraction wellheads, often at the same one per acre density.

As described in published U.S. Patent Application Number 20060034664, conventional gas extraction wells at landfills often involve deep wells attached to a network of pipes and a gas pump (blower) that applies vacuum (negative pressure) to extract the gas from the stored waste as the waste decomposes.

A prior art deep well arrangement according to the above published patent application is shown in FIG. 1. Landfill 1 containing waste 2 generates biogas (biogas flows shown by the arrows). Biogas is collected and extracted through a well 3. The well 3 includes a gas-collecting well screen 16 and a gas-impermeable conduit 17 linking the well screen to the surface to draw biogas from the wellhead to the surface. Overlaying the majority of the waste 2 is a gas-permeable layer 5. The term "wellhead" refers to a portion of the gas-extraction well from which gas can be extracted. The well often includes a section of pipe having slots or other gas-flow apertures cut in it, referred to as a "well screen". Often, the well screen is also surrounded with gravel.

The gas-permeable layer is typically composed of a conductive porous matrix with gas flow paths. Often it is composed of rigid or semi-rigid particles of a large enough size to leave a significant void volume between particles. For instance, the gas-permeable layer may contain sand, gravel, wood chips, or shredded tires. Above the gas-permeable layer is a gas-containment layer 7. Biogas that rises from the landfill reaches the gas-permeable layer where it is trapped by the overlying gas-containment layer 7. The biogas migrates horizontally in the gas-permeable layer until it comes close to a well. Gas extraction from the well creates a vacuum that draws gas into the well. This vacuum draws biogas from the overlying gas-permeable layer down through the waste mass of the landfill to reach the well.

The area immediately beneath the gas-permeable high conductivity layer 5 through which a substantial fraction of the biogas from the gas-permeable layer passes as it travels to the gas-collection wellhead is the entrainment zone 9. On its passage through the waste 2, the gas from the gas-permeable layer mixes with biogas produced in the waste mass that has not gone through the gas-permeable layer. This helps to give a consistent content to the biogas that is withdrawn from the well. If gas is withdrawn directly from the gas-permeable conductive layer, the gas composition will vary more dramatically over time, sometimes containing a high air content and sometimes not. It is sometimes desirable to place an even more impermeable layer, such as geomembrane 15, directly over the zone of entrainment of gas from the permeable layer that is created by the deep well. Moreover, sometimes the entire landfill is covered with such a membrane.

The deep well design of FIG. 1 is designed to pull gas away from the surface to protect the membrane cover from being impacted with gas buildup that can create ballooning. Typically, the deep well has a diminishing radius (zone) of influence as a result of pressure loss through the length of the well collector pipes. The deep well vacuum pressure pulls both gas and leachate into the well. Leachate pumps are often required, resulting in more membrane penetrations. The membrane cover helps alleviate air intrusion issues—however, multiple penetrations typically are required at each collection point. Membrane penetrations around wellheads are very susceptible to rips and tears the result in either gas leaks or air intrusion into the waste. Another drawback to the deep well is that the deep well must be continually monitored and adjusted. Deep wells normally utilize an adjustable valve at each collection point to control pressures within the well to adjust the radius of influence, but have limited maximum radius of influence from the control valve.

FIG. 2 shows another prior art arrangement, this time showing a more shallow wellhead 26 used to withdraw near-surface or sub-surface gas from beneath a membrane M capping a waste W. The wellhead 26 is attached to an above-ground conduit by way of a vertical pipe.

FIG. 3 shows another prior art arrangement, this time depicting a landfill with multiple wellheads 30 used to withdraw near-surface or sub-surface gas from beneath the surface. The wellheads 30 are attached to an above-ground vent 31.

FIG. 4 shows another prior art arrangement similar to that in FIG. 2, this time showing a field of wellheads 40 spaced to extract the gases from a landfill and collect the same. Such wellheads are often spaced about one per acre.

SUMMARY OF THE INVENTION

In an example form, the present invention relates to a gas collection grid for use at landfills and the like of the type having a gas-producing waste pile, the gas collection grid including a lower geocomposite positioned over the gas-producing waste pile. A protective layer of soil is positioned over the lower geocomposite, with a grid pattern of vertical openings formed in the protective layer of soil spaced apart from one another. An upper geocomposite is positioned over the protective layer of soil such that the protective layer of soil is positioned between the lower and upper geocomposites. An impermeable geomembrane is positioned over the upper geocomposite. A cruciform gas collector conduit grid is positioned within or atop the protective layer of soil and has a plurality of collection orifices formed adjacent the vertical openings formed in the protective layer of soil. The impermeable geomembrane is non-perforated adjacent the collection orifices and the cruciform gas collector conduit grid is adapted for delivering collected gas laterally from beneath the geomembrane rather than vertically through the geomembrane.

Preferably, the grid includes a series of space-apart shallow gas wells, with each including a lower geocomposite positioned over the gas-producing waste pile and a protective layer of soil positioned over the lower geocomposite. An upper geocomposite is positioned over the protective layer of soil such that the protective layer of soil is positioned between the lower and upper geocomposites. An impermeable geomembrane is positioned over the upper geocomposite and a shallow gas well collector is positioned within the protective layer of soil. Preferably, the shallow gas well includes a non-perforated outer pipe extending generally from the lower geocomposite toward the upper geocomposite. A perforated inner pipe is positioned within and extends within the non-perforated outer pipe and together with the non-perforated outer pipe defines a space between the two pipes. A quantity of gravel-like material is positioned within the space between the perforated inner pipe and the non-perforated outer pipe. A transport conduit extends beneath the geomembrane, and without extending through the geomembrane, for transporting gas produced by the waste pile and collected through the gravel-like material and into and through the perforated inner pipe of the shallow gas well collector.

In another example form, the present invention relates to a gas collection system for use at landfills and the like of the type having a gas-producing waste pile. The gas collection grid includes a protective layer of soil positioned over the waste pile, with a grid pattern of vertical openings formed in the protective layer of soil spaced apart from one another. An impermeable geomembrane is provided, as well as a gas collector conduit grid extending laterally beneath the impermeable membrane and positioned within or atop the protective layer of soil and having a plurality of collection orifices formed adjacent the vertical openings formed in the protective layer of soil. The impermeable geomembrane is non-perforated adjacent the collection orifices and the gas collector conduit grid is adapted for delivering collected gas laterally from beneath the geomembrane rather than vertically through the geomembrane.

Optionally, shallow gas wells are positioned at spaced apart points on the grid. The shallow gas wells can include a non-perforated outer pipe extending generally toward the geomembrane and a perforated inner pipe positioned within and extending within the non-perforated outer pipe and together with the non-perforated outer pipe defining a space between the two pipes. A quantity of gravel-like material can be positioned within the space between the perforated inner pipe and the non-perforated outer pipe. A transport conduit extends beneath the geomembrane and not through the membrane for transporting gas produced by the waste pile and collected through the gravel-like material and into and through the perforated inner pipe of the shallow gas well collector.

Optionally, a lower geocomposite is positioned over the gas-producing waste pile and an upper geocomposite is positioned over the protective layer of soil such that the protective layer of soil is positioned between the lower and upper geocomposites. Also optionally, an upper layer of soil is positioned between the gas collector conduit grid and the impermeable membrane. Preferably, the gas collector conduit grid is cruciform in general arrangement.

Advantageously, the above example forms of the present invention avoid perforations at the gas collection nodes/orifices. This eliminates a large number of perforations in the impermeable membrane, helping to maintain the structural integrity of the membrane and lengthening its effective service life.

In another example form, the present invention relates to a method of installing a gas collection grid for use at landfills and the like of the type having a gas-producing waste pile, the method comprising the steps of:
 a. covering the waste pile with a protective layer of soil;
 b. creating vertical openings in the protective layer of soil spaced apart from one another in a grid pattern;
 c. creating a cruciform grid of gas collector conduits having a series of gas collection orifices space apart from one another to generally match the spacing of the grid pattern of vertical openings in the protective soil layer and positioning the grid of gas collector conduits such that the orifices generally are aligned with the vertical openings in the protective soil layer;
 d. covering the grid of gas collector conduits with an upper layer of soil;
 e. placing a gas-impermeable membrane over the upper layer of soil; and
 f. connecting the grid of gas collector conduits with an external gas extraction apparatus.

BRIEF DESCRIPTION OF THE DRAWING FIGURES

DESCRIPTION OF EXAMPLE EMBODIMENTS

In an example form, the invention relates to a low-profile fluid collection well, such as for use at landfills and the like. In another example form, the present invention relates to a grid of gas collection wells and subsurface fluid conveyance conduit grid. Examples of these follow. In an example form, the collection grid extends laterally below the impermeable membrane, rather than vertically through it. In this example form of the present invention, the collection grid eliminates the need for perforations in the impermeable geomembrane at the gas collection nodes/orifices. This eliminates or avoids the need for a large number of perforations in the impermeable membrane, helping to maintain the structural integrity of the membrane and lengthening its effective service life.

Shallow Gas Well and Related Components

In one example form, the present invention relates to a sub-surface shallow gas well 50 for collecting and/or conveying sub-surface gas and the like from near the surface of landfills, typically for use with a geomembrane for capping a waste field. The geomembrane is generally impermeable to fluids in order to contain or cap the waste below, and thereby restrict the sub-surface gas from flowing into the atmosphere and to restrict atmospheric air from flowing into the waste below the geomembrane.

Figure 1:
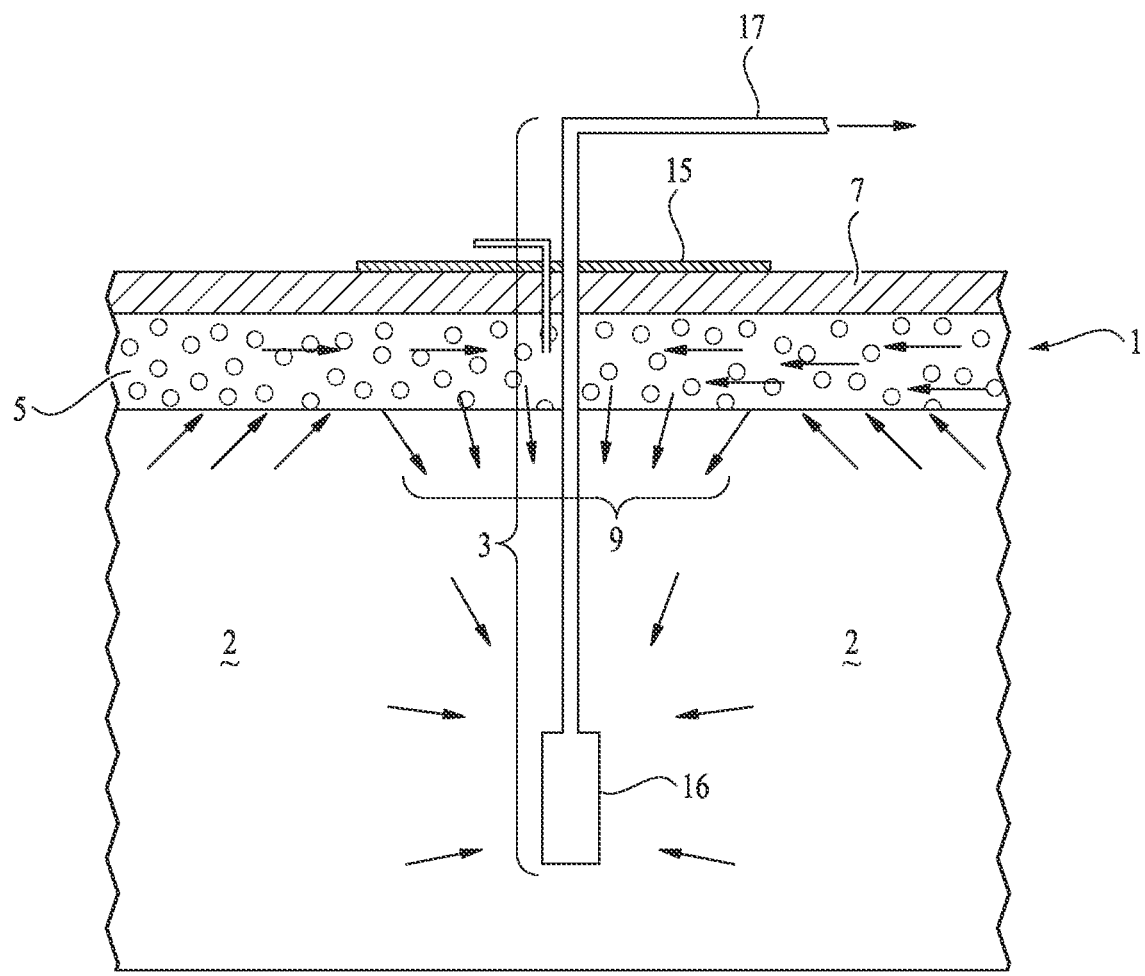
FIG. 1 is a schematic illustration of a first prior art wellhead for extracting sub-surface gas from a waste landfill.
Figure 2:
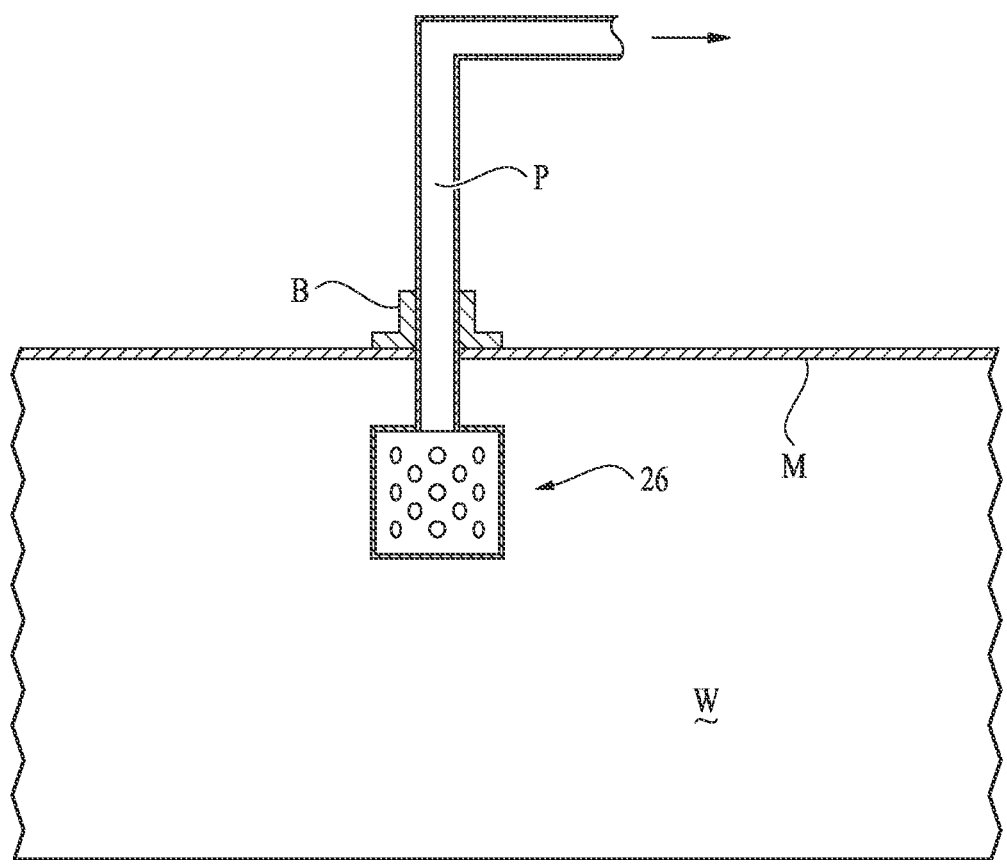
FIG. 2 is a schematic illustration of a second prior art wellhead for extracting sub-surface gas from a waste landfill.
Figure 3:
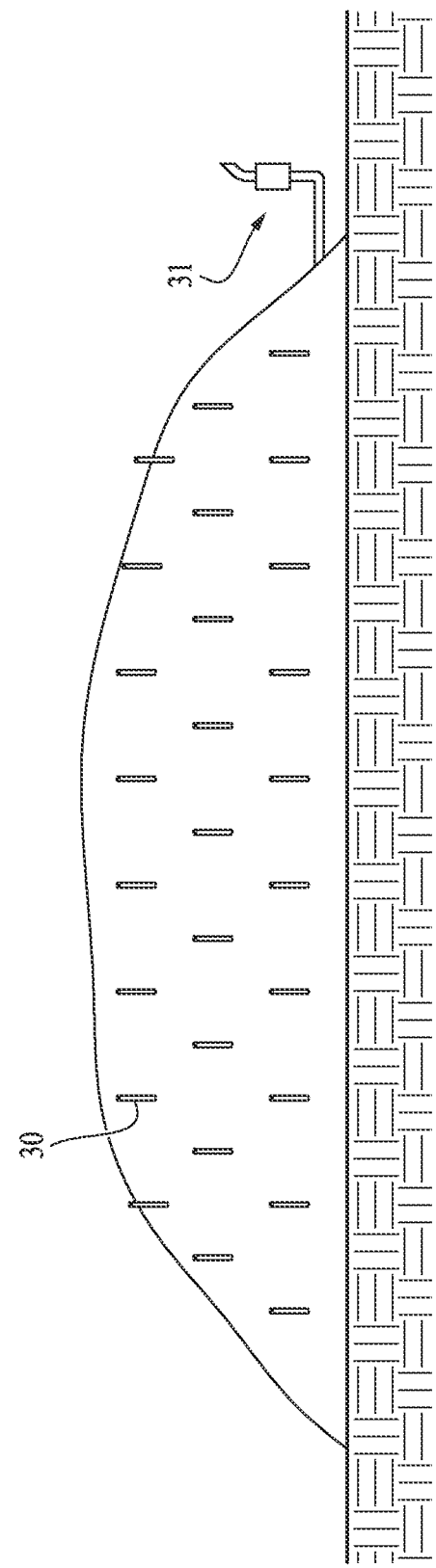
FIG. 3 is a schematic illustration of a prior art waste landfill with multiple wellheads for extracting sub-surface gas from a waste landfill.
Figure 4:
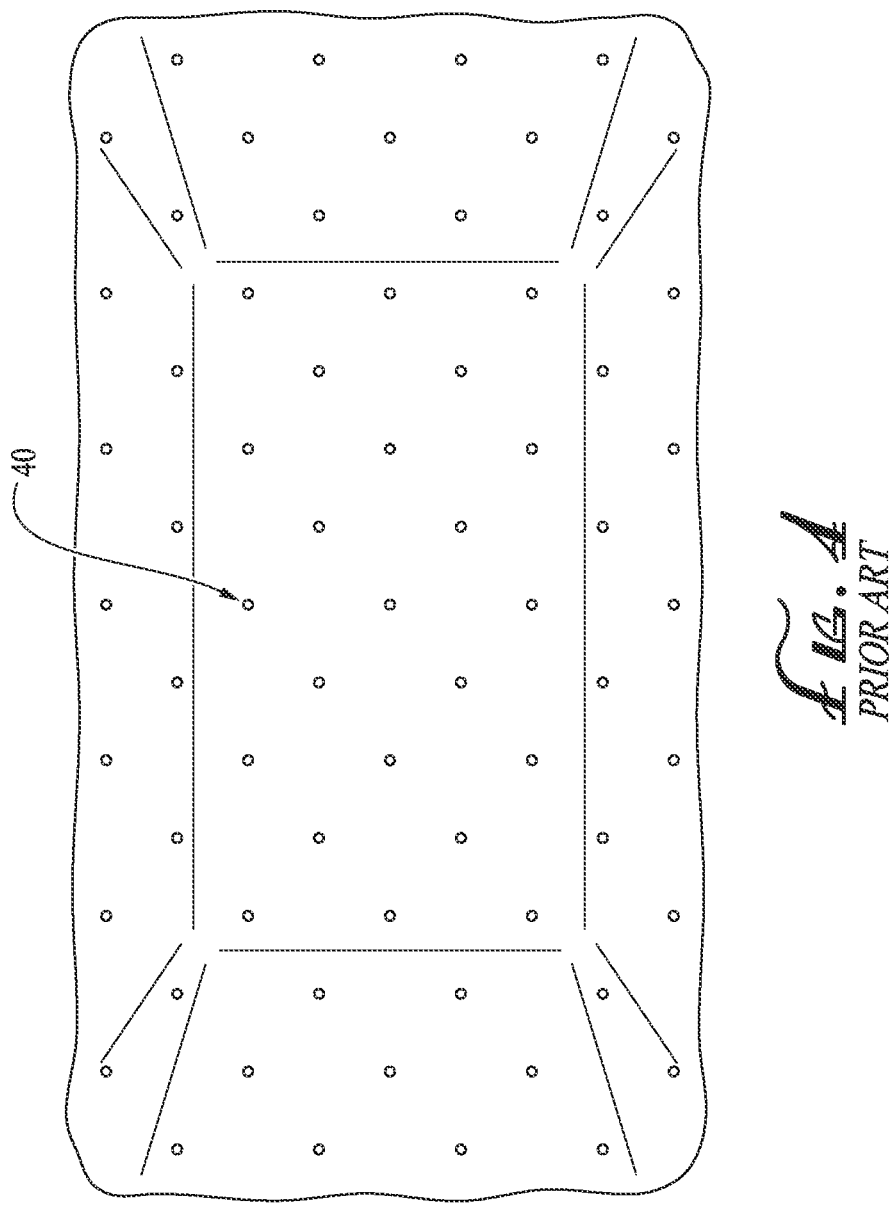
FIG. 4 is a schematic illustration of a prior art waste landfill with multiple wellheads for extracting sub-surface gas from a waste landfill.
Figure 5:
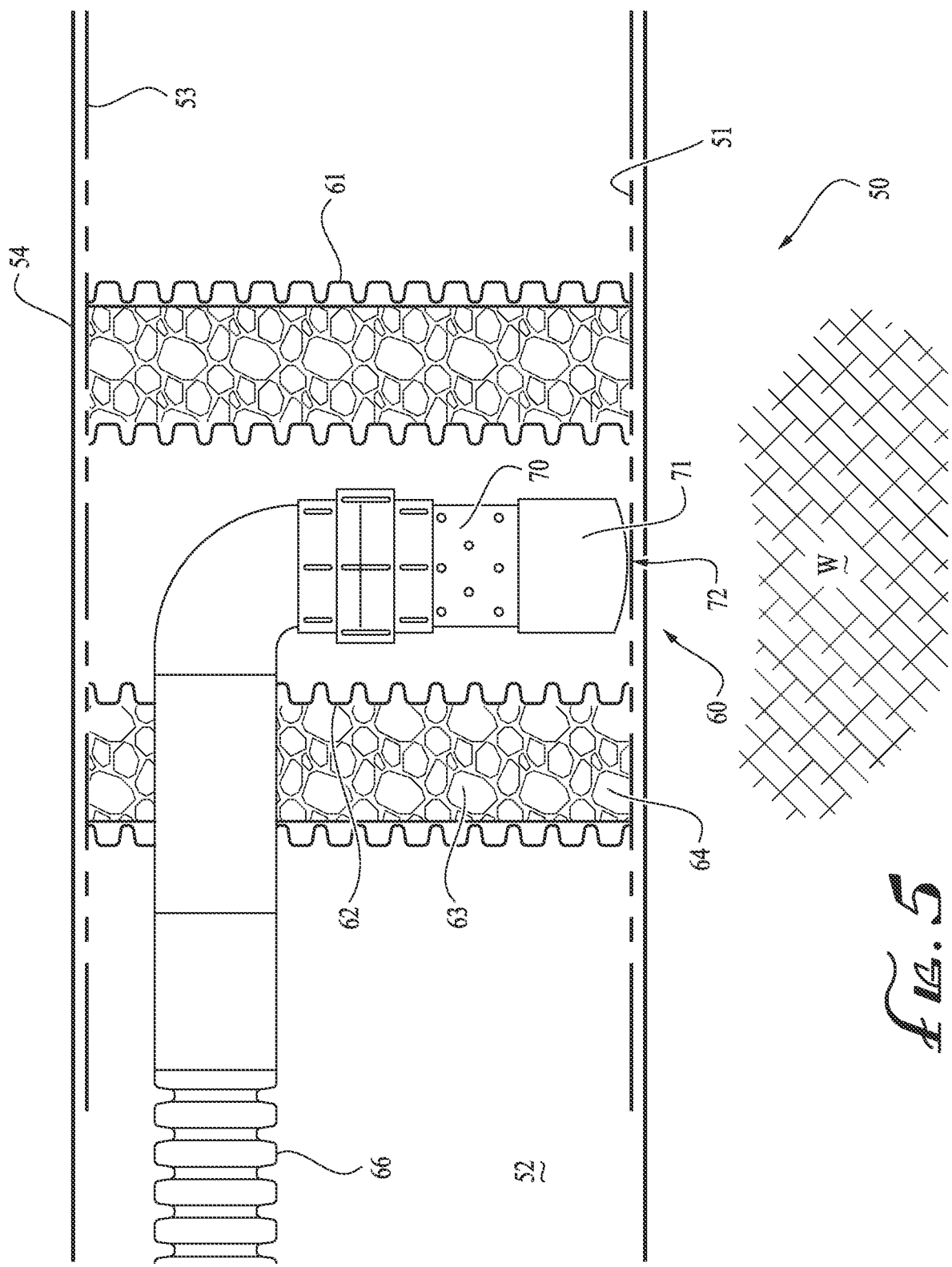
FIG. 5 is a schematic, sectional view of a shallow gas well for extracting and/or conveying sub-surface gas from a waste landfill according to a first preferred example form of the present invention.

FIG. 5 is a schematic, sectional view of the shallow gas well 50 for extracting and/or conveying sub-surface gas from a waste landfill according to a preferred example embodiment of the present invention. The shallow gas well 50 is for use at landfills and the like of the type having a gas-producing waste pile W. The shallow gas well 50 includes a lower geocomposite 51 positioned over the gas-producing waste pile W and a protective layer of soil 52 positioned over the lower geocomposite 51. Preferably, the protective soil layer can be between about 12 and 18 inches deep. An upper geocomposite 53 is positioned over the protective layer of soil 52 such that the protective layer of soil 52 is positioned between the lower and upper geocomposites 51, 53. An impermeable geomembrane 54 is positioned over the upper geocomposite 53 and a shallow gas well collector 60 is positioned within the protective layer of soil 52. Preferably, the shallow gas well 50 includes a non-perforated outer pipe 61 extending generally from the lower geocomposite 51 toward the upper geocomposite 53. As shown, the solid (non-perforated) outer pipe 61 can be corrugated, if desired. Likewise, the outer pipe 61 can be non-corrugated. A corrugated and perforated inner pipe 62 is positioned within and extends within the non-perforated outer pipe 61 and together with the non-perforated outer pipe defines a space 63 between the two pipes. A quantity of gravel-like material 64 is positioned within the space between the perforated inner pipe and the non-perforated outer pipe.

A transport conduit 66 extends beneath the geomembrane 54, and without extending through the geomembrane 54, for transporting gas produced by the waste pile W and collected through the gravel-like material 64 and into and through the perforated inner pipe 62 of the shallow gas well collector 60. The transport conduit 66 can be smooth, corrugated, or part smooth and part corrugate. As shown in this embodiment, the transport conduit 66 can be round pipe. Other shapes are possible, as will be discussed below.

Optionally, a perforated gas collector 70 is positioned within the perforated inner pipe and is connected in fluid communication with the transport conduit 66. Also optionally, the perforated gas collector 70 is capped at a lower end thereof with a cap 71 and the cap includes a drain 72 to allow condensate to drain out of the perforated gas collector 70.

Optionally, the gravel-like material 64 can be gravel. Also optionally, the gravel-like material 64 comprises shredded rubber or other materials that allow gas to flow therethough.

Optionally, the transport conduit can be in the form of round pipe. Alternatively, the transport conduit can be low-profile, short, flat conduit which is much wider than it is tall. Also, a combination of round pipe and flat conduit can be employed.

Figure 6:
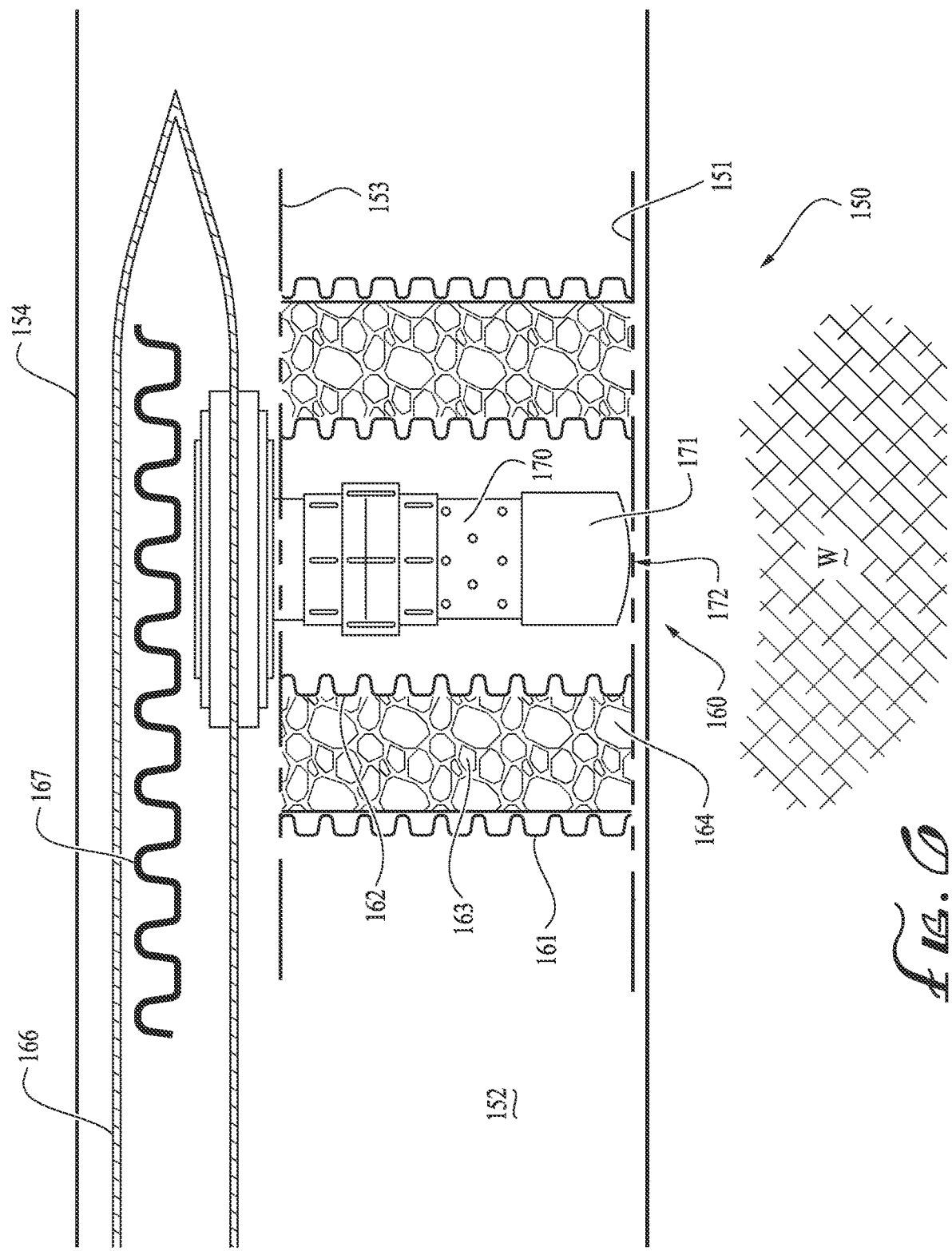
FIG. 6 is a schematic, perspective, partially cut-away view of a shallow gas well for extracting and/or conveying sub-surface gas from a waste landfill according to another preferred example form of the present invention.
Figure 7:
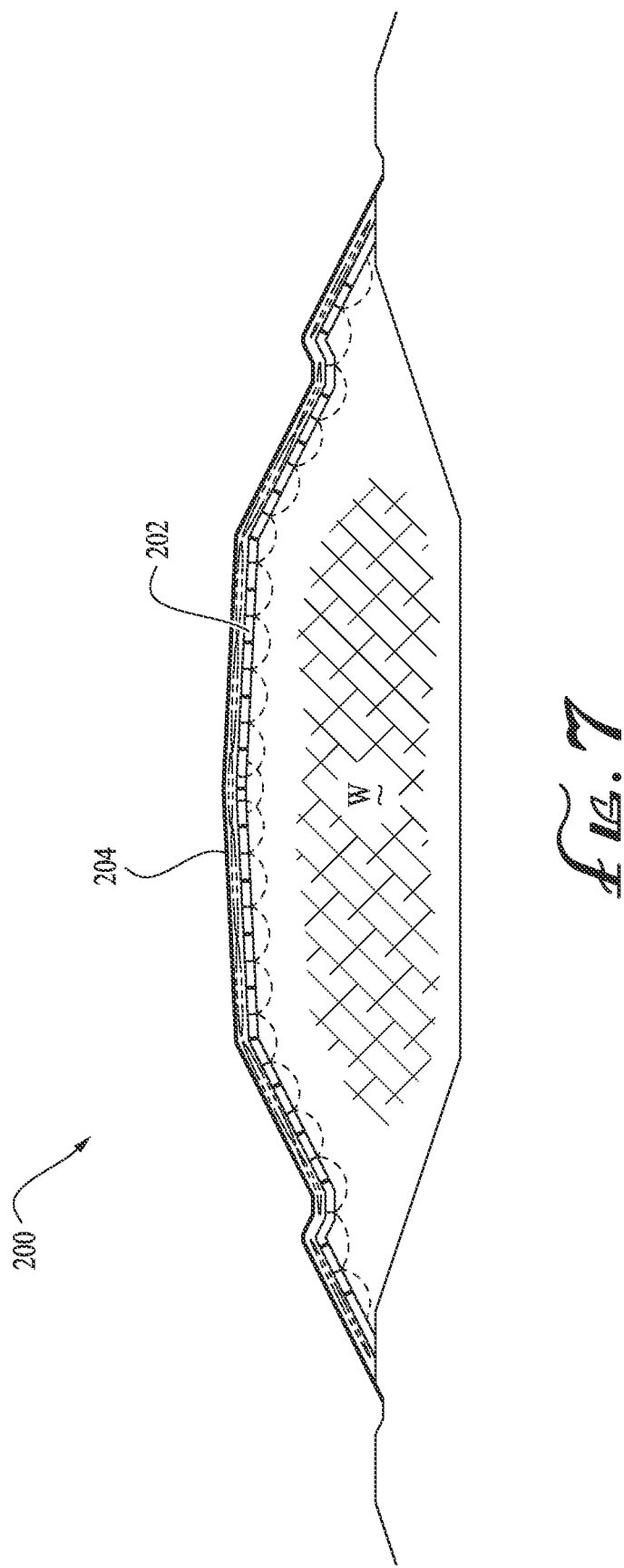
FIG. 7 is a schematic, sectional view of a collection grid of shallow gas wells for extracting and/or conveying sub-surface gas from a waste landfill according to another preferred example form of the present invention.
Figure 8:
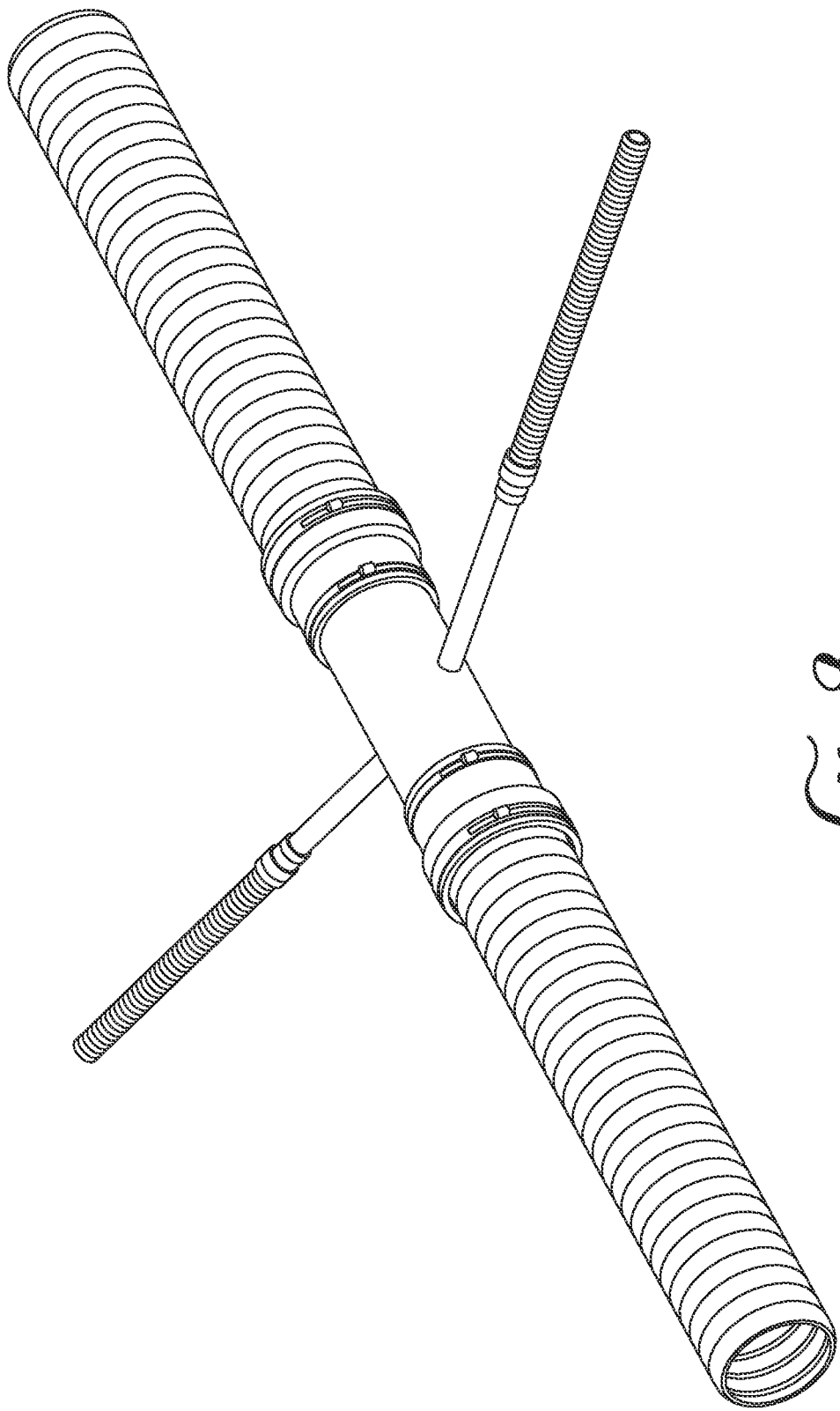
FIG. 8 is a schematic, perspective view of conduit portions of the collection grid of FIG. 7 in an example form of the present invention.
Figure 9:
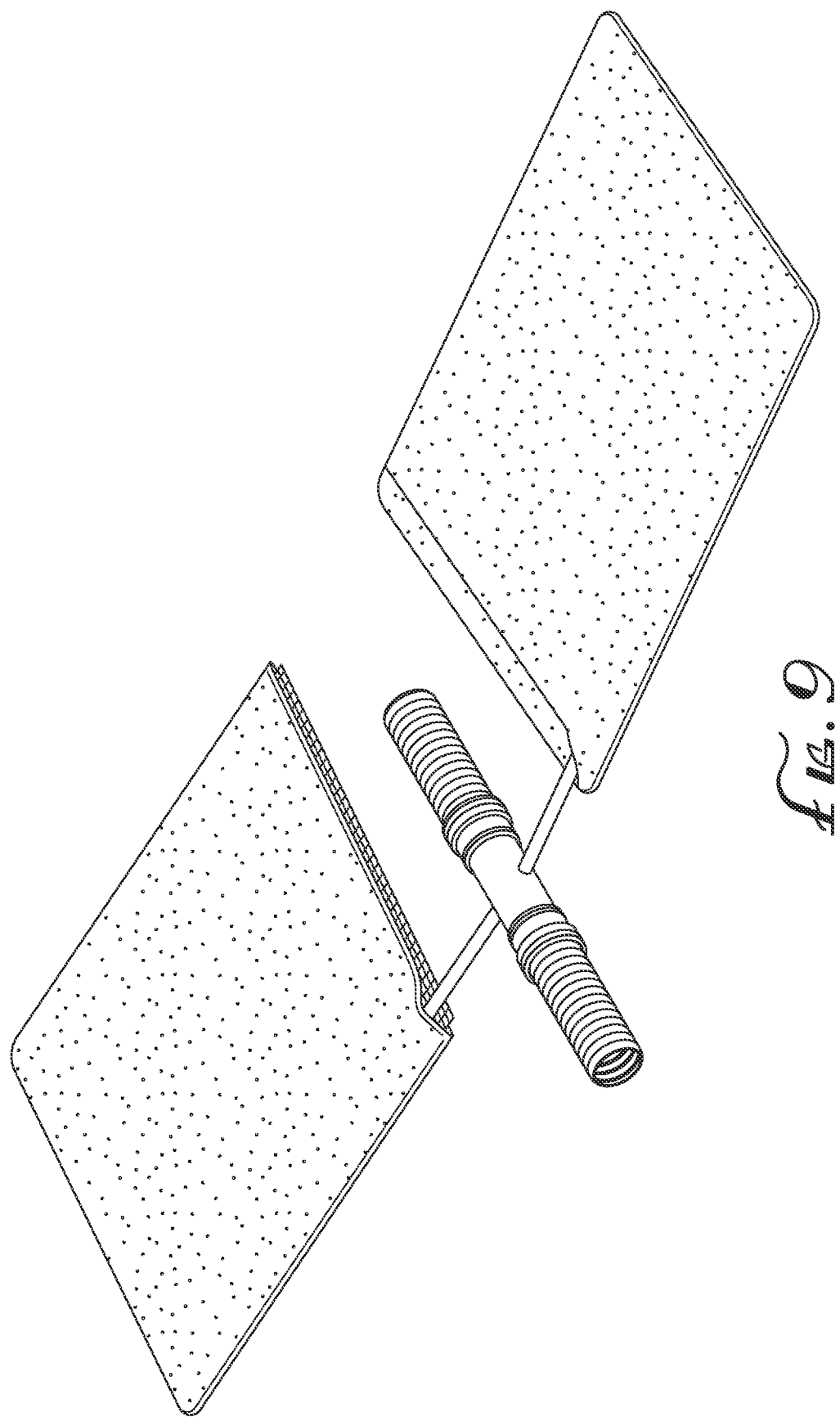
FIG. 9 is a schematic, perspective view of conduit portions of the collection grid of FIG. 7 in an example form of the present invention.
Figure 10:
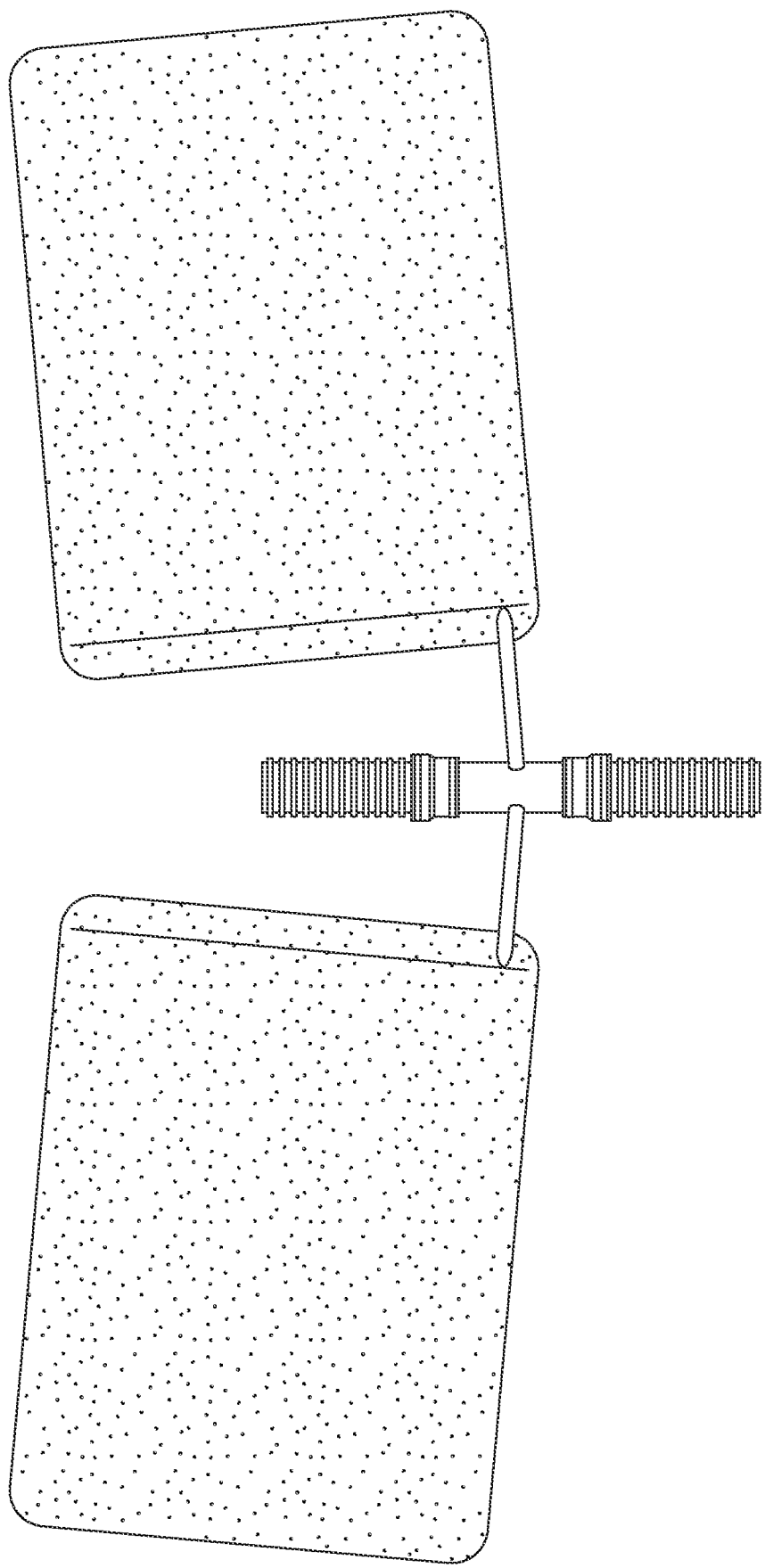
FIG. 10 is a schematic, top view of conduit portions of the collection grid of FIG. 7 in an example form of the present invention.
Figure 11:
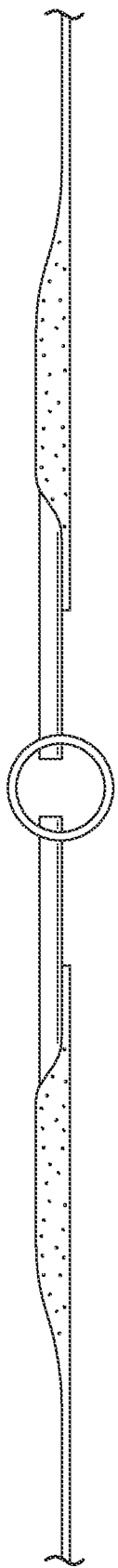
FIG. 11 is a schematic, end view of conduit portions of the collection grid of FIG. 7 in an example form of the present invention.
Figure 12:
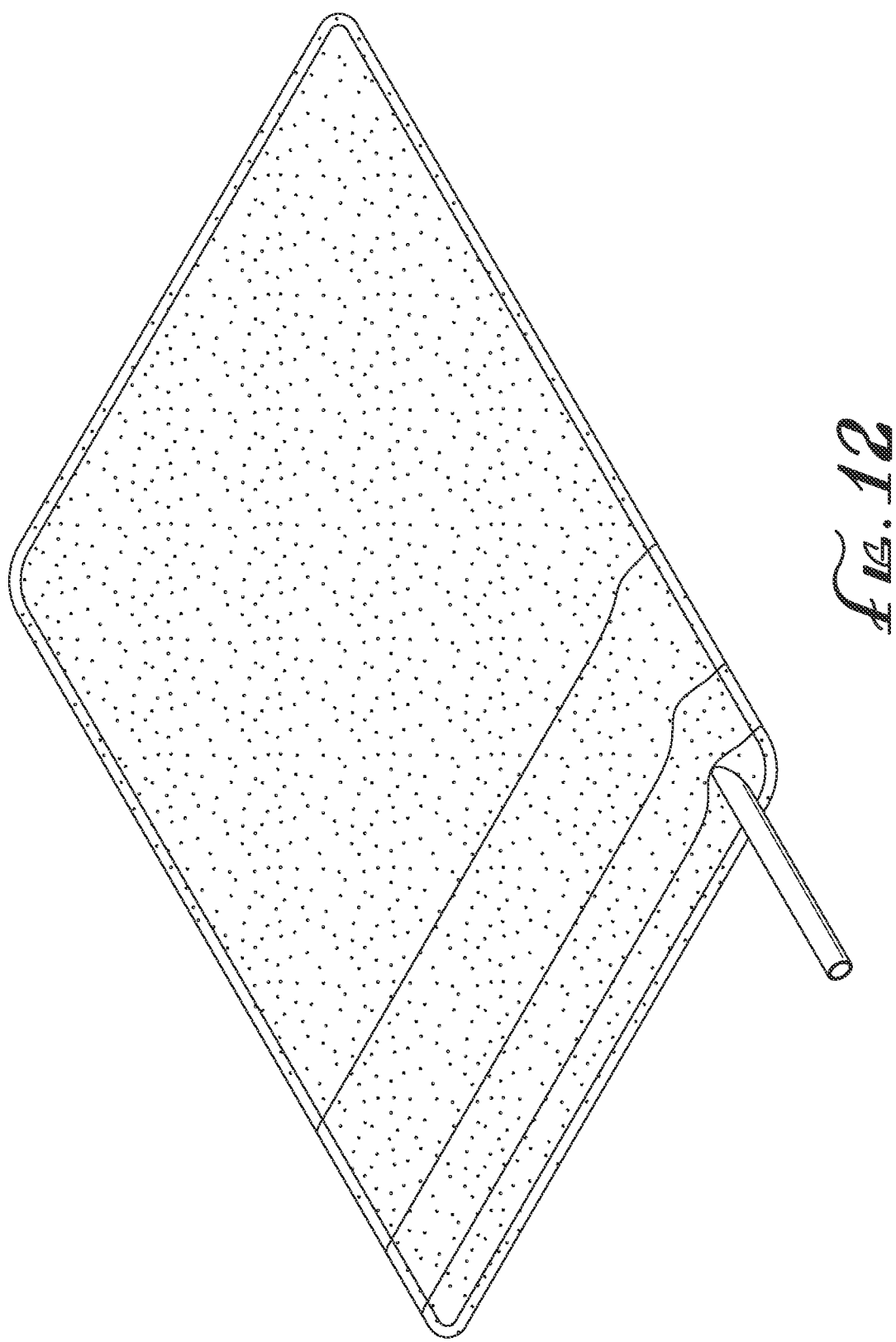
FIG. 12 is a schematic, perspective view of conduit portions of the collection grid of FIG. 7 in an example form of the present invention.
Figure 13:
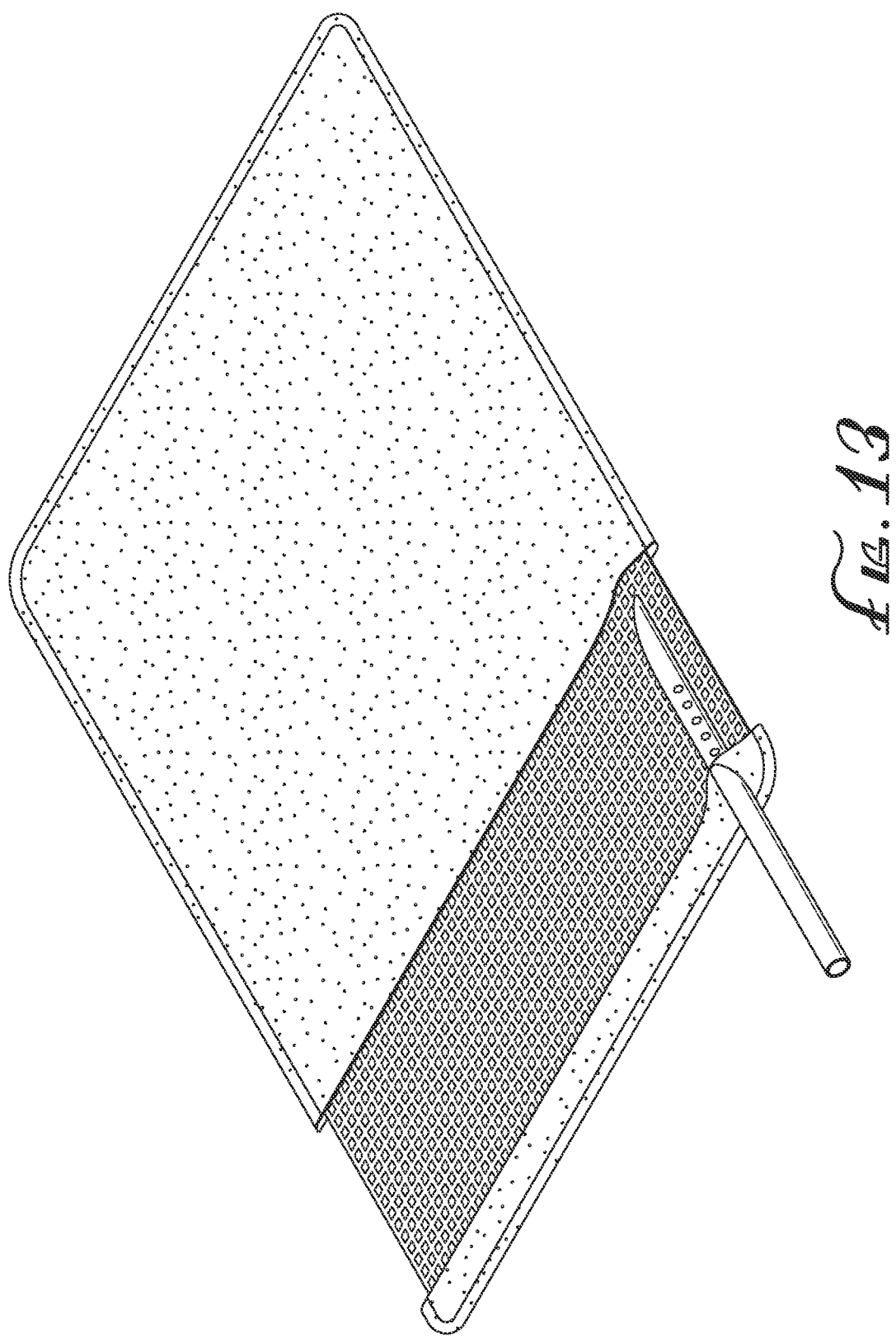
FIG. 13 is a schematic, perspective partially exploded view of conduit portions of the collection grid of FIG. 7.

FIG. 6 shows another form of a shallow gas well 150 for extracting and/or conveying sub-surface gas from a waste landfill according to another preferred example embodiment of the present invention. The shallow gas well 150 is for use at landfills and the like of the type having a gas-producing waste pile W. The shallow gas well 150 includes a lower geocomposite 151 positioned over the gas-producing waste pile W and a protective layer of soil 152 positioned over the lower geocomposite 51. Preferably, the protective soil layer 152 can be between about 12 and 18 inches deep. An upper geocomposite 153 is positioned over the protective layer of soil 152 such that the protective layer of soil 152 is positioned between the lower and upper geocomposites 151, 153. An impermeable geomembrane 154 is positioned over the upper geocomposite 153 and a shallow gas well collector 160 is positioned within the protective layer of soil 52. Preferably, the shallow gas well 150 includes a non-perforated outer pipe 161 extending generally from the lower geocomposite 151 toward the upper geocomposite 153. As shown, the solid (non-perforated) outer pipe 161 can be corrugated, if desired. Likewise, the outer pipe 161 can be non-corrugated. A corrugated and perforated inner pipe 162 is positioned within and extends within the non-perforated outer pipe 161 and together with the non-perforated outer pipe defines a space 163 between the two pipes. A quantity of gravel-like material 164 is positioned within the space between the perforated inner pipe and the non-perforated outer pipe.

A transport conduit 166 extends beneath the geomembrane 154, and without extending through the geomembrane 154, for transporting gas produced by the waste pile W and collected through the gravel-like material 164 and into and through the perforated inner pipe 162 of the shallow gas well collector 160. The transport conduit 166 can be smooth, corrugated, or part smooth and part corrugated. As shown in this embodiment, the transport conduit 166 can a flat, wide, shallow pipe and can have internal ribs 167 or other structure to keep the pipe from collapsing. As shown in this example, the internal ribs 167 can take the form of a "J-drain".

Optionally, a perforated gas collector 170 is positioned within the perforated inner pipe and is connected in fluid communication with the transport conduit 166. Also optionally, the perforated gas collector 170 is capped at a lower end thereof with a cap 171 and the cap includes a drain 172 to allow condensate to drain out of the perforated gas collector 170.

A Shallow Gas Well Collection Grid

In another example form, the present invention relates to a collection grid 200 of shallow gas wells for use at landfills and the like of the type having a gas-producing waste pile. The shallow gas wells can be of the general designs described above and shown in FIGS. 5 and 6 and can be connected to one another in fluid communication and the collected gas can be drawn away by one or more pumps. The shallow gas wells include a lower geocomposite positioned over the gas-producing waste pile W and a protective layer of soil 202 positioned over the lower geocomposite. An upper geocomposite is positioned over the protective layer of soil such that the protective layer of soil 202 is positioned between the lower and upper geocomposites. An impermeable geomembrane is positioned over the upper geocomposite and a large number shallow gas well collectors are positioned within the protective layer of soil. The shallow gas well collectors include a non-perforated outer pipe extending generally from the lower geocomposite toward the upper geocomposite and a perforated inner pipe positioned within and extending within the non-perforated outer pipe and together with the non-perforated outer pipe defining a space between the two pipes. A quantity of gravel-like material is positioned within the space between the perforated inner pipe and the non-perforated outer pipe. A transport conduit extends beneath the geomembrane and without extending through the membrane for transporting gas produced by the waste pile and collected through the gravel-like material and into and through the perforated inner pipe of the shallow gas well collector.

Optionally, the shallow gas wells each have a perforated gas collector positioned within the perforated inner pipe and connected in fluid communication with the transport conduit. Preferably, the shallow gas wells each are capped at a lower end of the perforated gas collector with a cap and the cap includes a drain to allow condensate to drain out of the perforated gas collector.

Optionally, the gravel-like material in the shallow gas wells comprises gravel. Alternatively, the gravel-like material in the shallow gas wells can be shredded rubber or other material that allows gas to flow through the material.

Optionally, the transport conduits comprise round pipe. Alternatively, the transport conduits can be low-profile, short, flat conduits which are much wider than tall. Further, a combination of round pipe and flat conduits can be employed.

As shown in FIG. 8-13, preferably, the grid is substantially cruciform in shape and at intersections of various conduits an adapter T or cross is provided. Preferably, the grid includes at least one trunk conduit and the at least two branch conduits each comprise an elongate, non-perforated outer cover. Optionally, the at least four collector conduits each comprise an elongate perforated outer cover.

In the case of using a flat, wide conduit, a box-like outer casing forming an enclosure with a substantially flat upper portion, a flat lower portion, and defining an interior volume. The casing can include, or not include, perforations formed therein to provide for the admission of sub-surface gas into the interior volume, as desired. Preferably, the outer casing comprises a fluid-impermeable membrane and the interior volume 55 provides an inner gas or fluid flow channel. Optionally, an upper orifice or inlet opening 58 is formed in the upper portion of the enclosure or casing.

Preferably, the outer casing is thin, and forms a conduit with a large aspect ratio of width to height. Also, the conduit is adapted to be quite long and the interior volume is supported and maintained with the aid of a reinforcement corrugation J-drain). The corrugation serves to provide structural rigidity and integrity against collapse, in order to maintain an open flow volume, despite forces that may otherwise tend to crush the casing. Preferably, the elongate outer cover is much thinner than it is tall and is flexible. Preferably, the elongate outer cover is made from one or more polymers. Preferably, the elongate outer cover has an aspect ratio of width to height of more than 10:1. More preferably, the elongate outer cover has an aspect ratio of width to height of more than 20:1. In a preferred example, the elongate outer cover has an aspect ratio of width to height of more than 50:1. Optionally, the elongate outer cover has a height of between about ½ inch and about 3 inches. More preferably, the elongate outer cover has a height of about one inch. Optionally, the elongate cover can have a width of between about one foot and about 8 feet. So for example, the cover can be a foot wide, two feet wide, 3.5 feet wide, 4 feet wide, 6 feet wide, etc.

The sub-surface gas to be collected and withdrawn with the present invention can be any of several sub-surface gases, such as natural gas. The fluid collected and conveyed can be gaseous or liquid.

The gas well grid can include a graduated conveyance grid with at least one high-volume, low-profile fluid trunk conduit. It also can include at least two medium-volume, low-profile fluid branch conduits connected to and feeding into the at least one high-volume, low profile trunk conduit. Further, it can include at least four lower-volume, low-profile collector conduits connected to and feeding into the at least two medium-volume, low profile branch conduits, with each branch conduit being connected to at least two of the collector conduits. With this construction, gas can be drawn into the smaller collector conduits, gathered into the somewhat larger branch conduits, and finally into the trunk conduit.

Optionally, the fluid conveyed within the conveyance conduit grid includes at least some water. Optionally, the fluid includes surficial landfill gas. Optionally, the grid is adapted for use under the surface of a landfill, with the grid further comprising an impermeable membrane positioned under the surface of the landfill and over the conduits.

Preferably, the grid is substantially cruciform in shape and at intersections of various conduits an adapter T or cross is provided. Optionally, the adapter T or cross has an upper opening and is provided with a cover for covering the upper opening.

Preferably, the grid includes at least one trunk conduit and the at least two branch conduits each comprise an elongate, non-perforated outer cover. Optionally, the at least four collector conduits each comprise an elongate perforated outer cover.

Preferably, the elongate outer cover comprises a polymer.

Preferably, the collector conduits have an aspect ratio of width to height of more than 10:1. More preferably, the aspect ratio is more than 20:1. Indeed, even an aspect ratio of more than 50:1 can be achieved.

The system design, coupled with a membrane cover, creates a superior barrier and conveyance system for gas emissions. The radius of influence of the system can be every square foot between the waste mass and the atmosphere.

The system requires no drilling (wells), no trenching (buried piping), and no above-ground piping. It also produces no condensate, and allows for a significant reduction in effort in monitoring of collection points. Advantageously, it avoids the typical perforations at the deep well collection points, thereby minimizing the perforations in the impermeable membrane. In some cases, it may be useful to provide pressure relief valves that extend vertically through the membrane. But even in such circumstances, using a collection grid that extends laterally beneath the membrane, rather than vertically through the membrane, is nonetheless helpful for minimizing the overall number of perforations created in the membrane.

The system is a designed and manufactured solution that provides for an easy and quick installation of a gas collection system that requires reduced capital costs, lowered O&M costs, stability in gas collection management along with a significant reduction in condensate generation.

The shallow gas well collection system is designed specifically for both long and short-term interim cover areas. The system creates a semi-conical radius of influence into the waste mass and a linear radius of influence between the impermeable membrane and protective cover layer. The shallow gas well system creates barriers of both an impermeable membrane and vacuum in an area of the landfill that is critical to preventing fugitive emission from escaping into the environment.

The system alleviates the high costs and maintenance associated with deep well gas collection designs and the low performance characteristics of horizontal collectors as well as the multiple membrane penetrations associated with both deep well and surficial gas collection systems. To accomplish this, a radius of influence across a large area is created by ensuring an available vacuum pressure is sustained throughout the shallow gas well gas collection system with an overlying impermeable membrane. This is achieved by utilizing the sites-specific gas generation rate modeling to determine how much gas will need to be collected from an area. The estimated gas volume and the collection area size are then calculated along with the available vacuum, industry standards for friction loss in gas conveyance to determine the size of each orifice in the shallow gas well's flux chamber.

Preferably, there is no need for overlying membrane penetrations at the individual shallow gas well gas collection points. Preferably, each shallow gas well (see FIGS. 5-13) collection point has a flux chamber that penetrates through the protective soil layer and onto the top of the underlying waste mass. The flux chamber is made up of a larger diameter solid outer pipe with smaller diameter perforated pipe. The area between the two is filled with a highly permeable material such as gravel. The interior portion of the smaller diameter is where both the orifice, collector and condensate drain reside.

Gas is conveyed from each shallow gas well collection point across the field into appropriately sized laterals for gas volumes that intersect into an appropriately sized single trunk. Each trunk/lateral set is called a collection tree and is designed to provide a very large radius with a single membrane penetration at a connection point with the main gas header system. The Shallow Gas Well collection system is designed as a double barrier for gas control in that the piping network contain and convey the necessary available vacuum pressures across the field while the overlying membrane contains the gas being generated within the landfill. The system design anticipates an equilibration of pressure loss and gas generation rate differences across the collection field that results in a very stable and consistent gas collection method. All gas generation models are theoretical at best and cannot truly and accurately predict the gas generated within a specified area, therefore with prior art, there has always been a need for an adjustable valve and monitoring ports at each collection point.

The EF system is designed for easy installation as well as easy removal and reutilization in other parts of the landfill. Other prior art gas systems are unrecoverable for reutilization and have a limited life span of use.

The illustrative embodiments of the present invention can take advantage of the inventor's new understanding of flux in determining the status of flux for specific landfill gas collection systems. To begin, let's first describe the results of flux. Flux can be explained in three distinctly different results. The first is negative flux, which is described as high input and low output. The second is zero flux, which is described as same input and same output. Thirdly, positive flux is described as low input and high output.

As we consider gas flux in a landfill setting, the input value is the gas generation rate of the landfill and the output value is the gas collection rate of the specific landfill gas collection system type. Additionally, for this discussion, ballooning of membrane would create a Negative flux, inefficient collection can create a Positive Flux and leaks create a Negative Flux. Each landfill or portion of a landfill typically will be in one of the categories of flux as previously mentioned. So, based upon our criteria of gas generation versus gas collected to determine flux category.

1. Gas generating landfill with no gas system—Negative Flux (leaks through soil)
2. Gas generating landfill with vents—Negative Flux (leaks through vents and soil)
3. Gas generating landfill with dirt and deep wells—Negative Flux (leaks through soil)
4. Gas generating landfill with membrane cover and deep wells—Zero Flux and Positive Flux (collection meets production, deep wells unnecessary to achieve Zero Flux)
5. Gas generating landfill with horizontal gas collection trenches with soil cover—Negative Flux (leaks through soil)
6. Gas generating landfill with horizontal gas collection trenches with membrane cover—Negative Flux (unable to sustain vacuum over large areas, unreliable collection)
7. Gas generating landfill with surficial gas collection with membrane—Zero Flux (positive pressure from continuous gas generation pushes gas to the collection zone)

8. Gas generating landfill with shallow gas collection wells and membrane—Zero Flux. (positive pressure from continuous gas generation pushes gas to the collection zones)

As one can see from the above, the only systems that have an ability to reach near Zero Flux are the systems with a membrane cover. While radius of influence has always been the goal of gas system designers, the present inventor introduces the idea that radius of influence is less important than achieving near Zero Flux.

Advantageously, the present invention can achieve: 1. Increased radius of influence for gas collection per membrane penetration (whether round pipe of flat pipe, very important); 2. Shallow well gas collection. (flux chamber, collector and orifice); 3. Sustainable available vacuum pressure across a large collection area below a membrane (pre-designed orifice sizing matched to the specific landfill's gas generation modeling); 4. A dual environmental shield to fugitive emissions. First, an impermeable membrane. Secondly, a vacuum barrier between the underlying soils and the overlying impermeable membrane. (Our radius of influence is linear and semi-conical); 5. A gas collection system that is self-balancing as a result of the dual radius of influence and the goal of designing the available vacuum pressures across the collection field to be in a zero flux balance between the gas collection capacity and the underlying waste gas generation rate.

Optionally, one can utilize a spreadsheet capable of building out the system requirements as in relation to pipe type, pipe size and orifice size for each collection point based upon the site's specific gas generation modeling and the area to be under the influence of this system.

Figure 14:
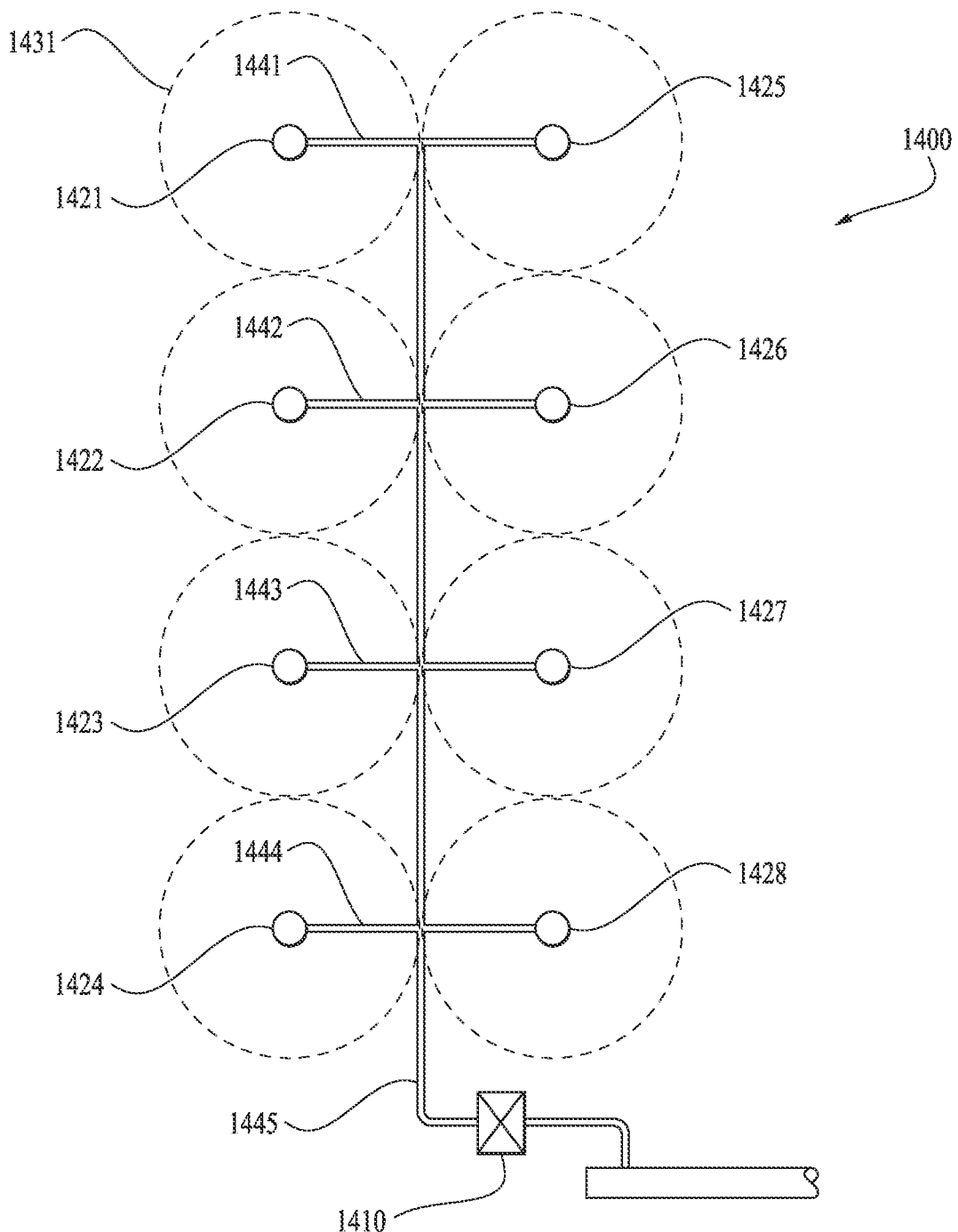
FIG. 14 is a schematic, plan view of a Gas Management Cover System, including a collection grid of shallow gas wells for extracting and/or conveying sub-surface gas from a waste landfill according to another preferred example form of the present invention.
Figure 15:
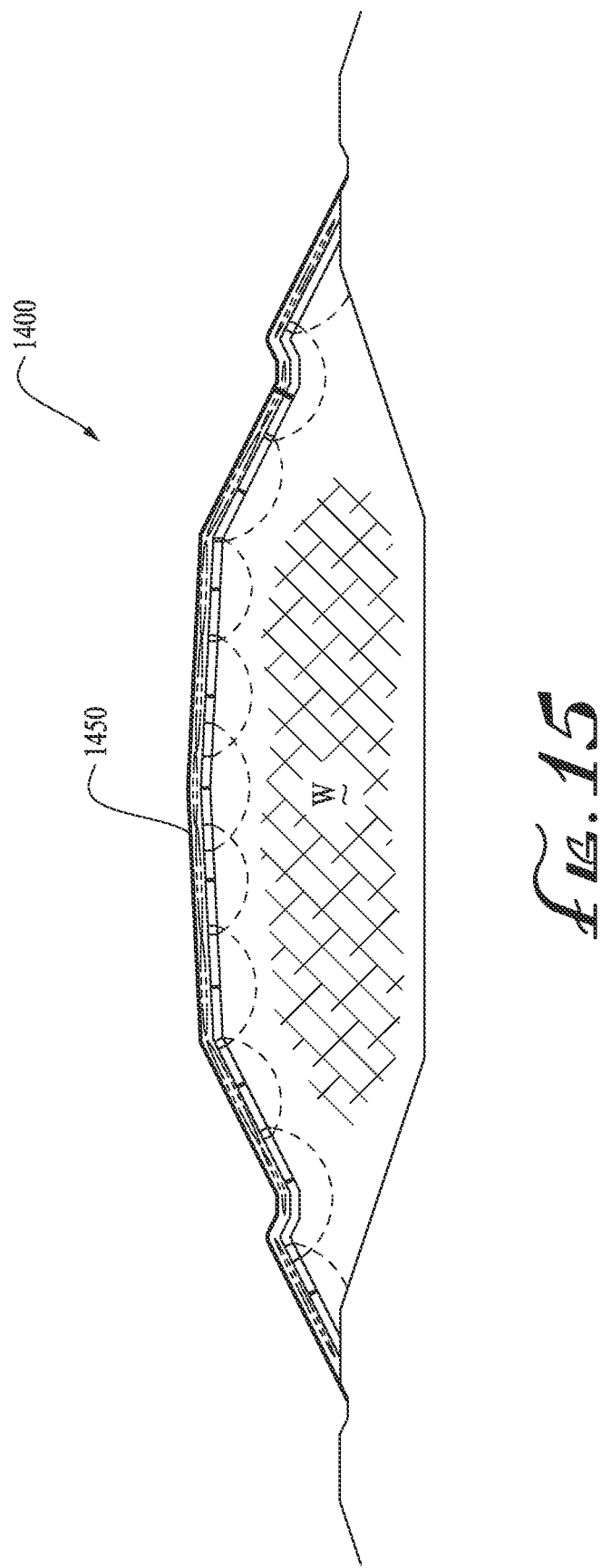
FIG. 15 is a schematic, sectional view of portions of the collection grid of FIG. 14 in an example form of the present invention.

FIG. 14 shows a gas management cover system 1400 designed preferably for short to long term intermediate cover areas that require efficient and cost effective methods for controlling fugitive emissions. The system consists of four main or primary components to create a high-performance system capable of collecting landfill gas. One main component is an automatic isolation valve 1410. This isolation valve allows gas to be pulled from the gas management cover system. During normal operation, it automatically shuts and isolates the system in the event that the gas management cover system shuts down to prevent gas from backflowing.

The gas management cover system 1400 also includes a series of shallow collection wells 1421-1428. Preferably, each of these shallow gas collection wells is designed to create a radius or zone of influence, such as 1431, from or into the underlying waste mass as well as directly beneath the geomembrane. The shallow gas collection wells do not require either an adjustable valve or a geomembrane penetration at the collection point. Thus, they are able to maintain vacuum across large areas. Preferably, these shallow gas collection wells are designed for quick installation without requiring specialty drilling rigs.

The cover system 1400 also includes pressure relief valves installed across the gas management cover system area. Typically, these are installed at a density of about 1 per acre, depending upon the gas generation projections for the particular waste mass. The valves prevent air from being pulled into the gas management cover system during normal gas collection operations and are designed to open and relieve gas pressure during periods when the primary gas collection control system is not working or is not working correctly. The pressure relief valves are spread out across the collection area to address both the safety of the geomembrane from ballooning and an even dispersal of gas across a large area, much the same as gas moves through soil covers during periods of time when the primary gas management cover system is not functioning.

The gas management cover system 1400 also includes shallow gas lateral system components 1441-1445. The collection laterals are buried just under the surface of the soil and utilize single-wall corrugated piping systems to connect the shallow gas collection miles. The lateral system is designed for quick installation without requiring plastic pipe welding.

The geomembrane 1450 preferably is a 35-mil geomembrane with an engineered profile structure to hold an upper layer in place. The geomembrane addresses or prevents water infiltration into the landfill and controls fugitive emissions from the landfill. It also minimizes the surface water contamination and erosion.

An upper layer component 1460 is installed on top of the geomembranes to compensate for wind loading. The top layer combines with the underlying geomembrane to provide a safe walking surface and provide an appealing or good looking installation. The upper layer can take the form of a synthetic turf or another woven or non-woven product.

Figure 16:
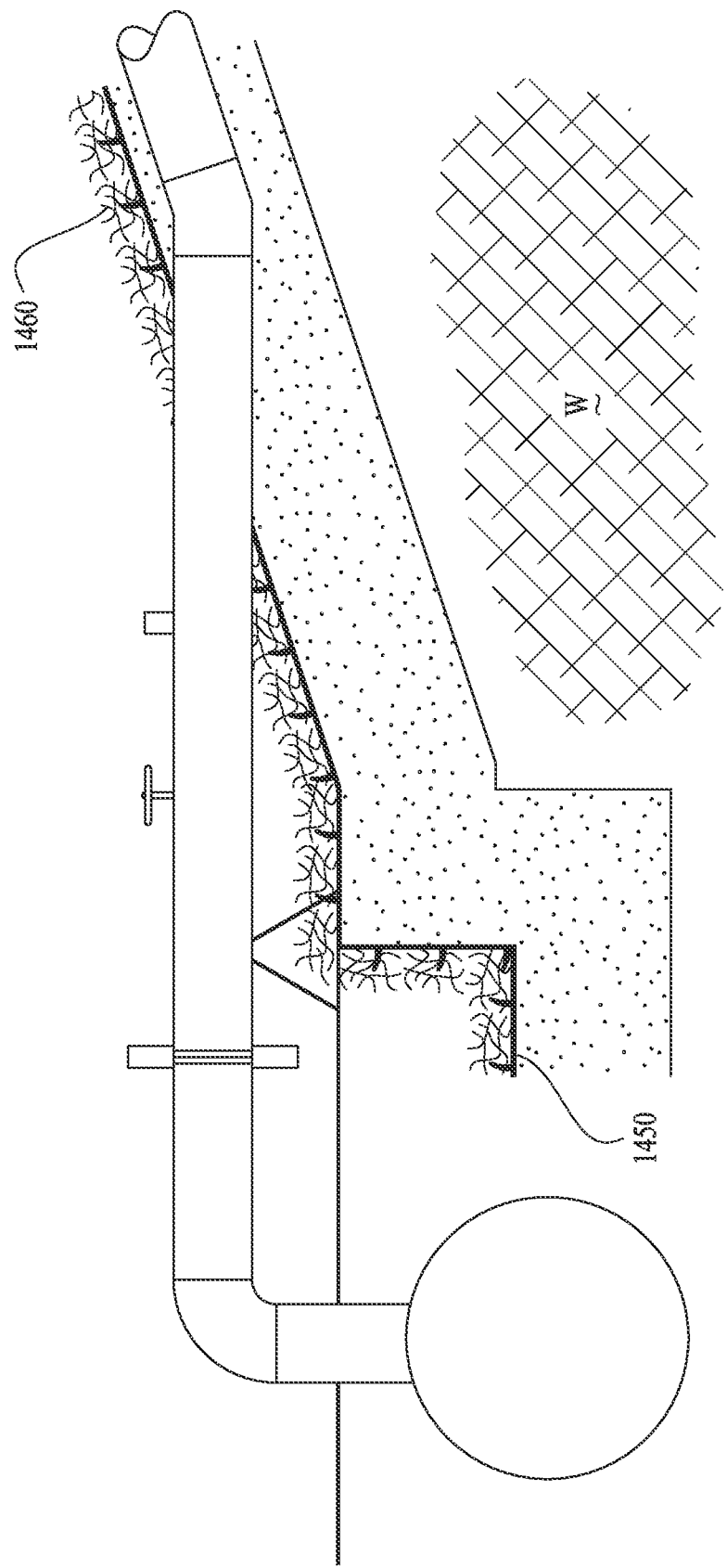
FIG. 16 is a schematic, sectional view of conduit portions and other portions of the collection grid of FIG. 14 in an example form of the present invention.
Figure 17A:
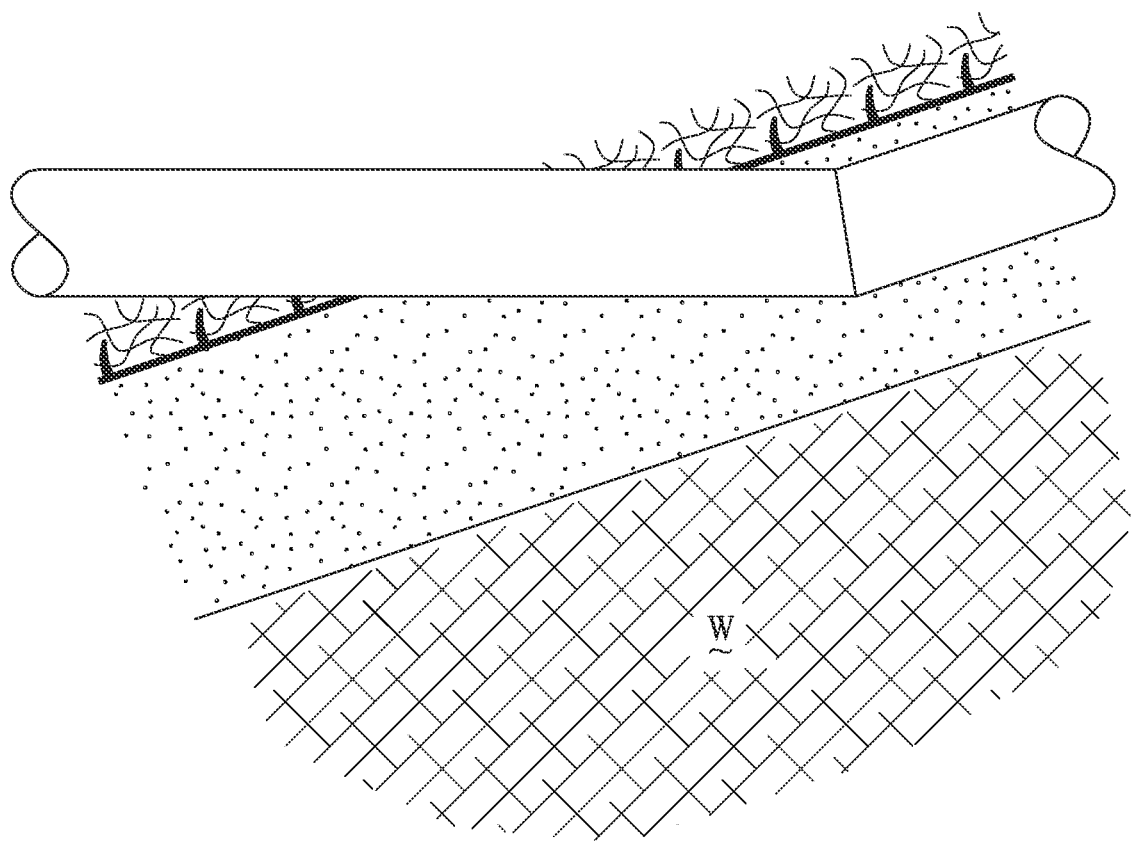
FIG. 17A is a schematic, sectional view of conduit portions of the collection grid of FIG. 16 in an example form of the present invention.
Figure 17B:
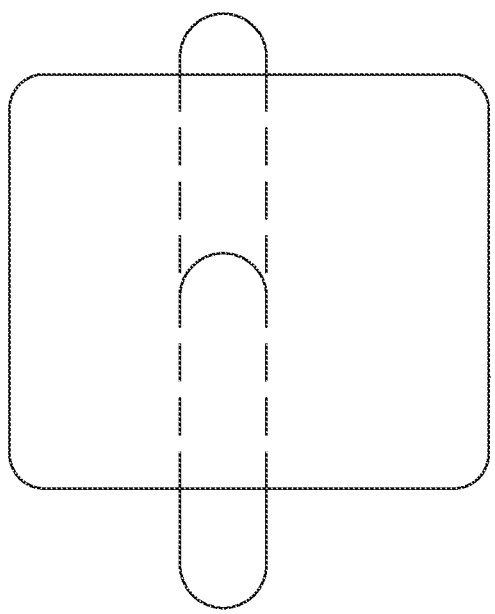
FIG. 17B is a schematic, plan view of conduit portions of the collection grid of FIG. 17A in an example form of the present invention.

As shown in FIG. 16, a shallow gas collection pipe can be made from high density polyethylene. The shallow gas collection pipe can be embedded in the protective cover and can emerge therefrom through a pipe boot as desired. The protective cover, as previously described, sits beneath a 35 mil geomembrane and an upper layer. The shallow gas collection pipe can include one or more sampling ports, if needed. Further, the shallow gas collection pipe includes a manual valve and rests upon optional pipe saddles. The shallow gas collection pipe includes an automatic isolation valve upstream of the main gas header conduit. All of this sits atop the waste pile, as depicted.

Figure 18:
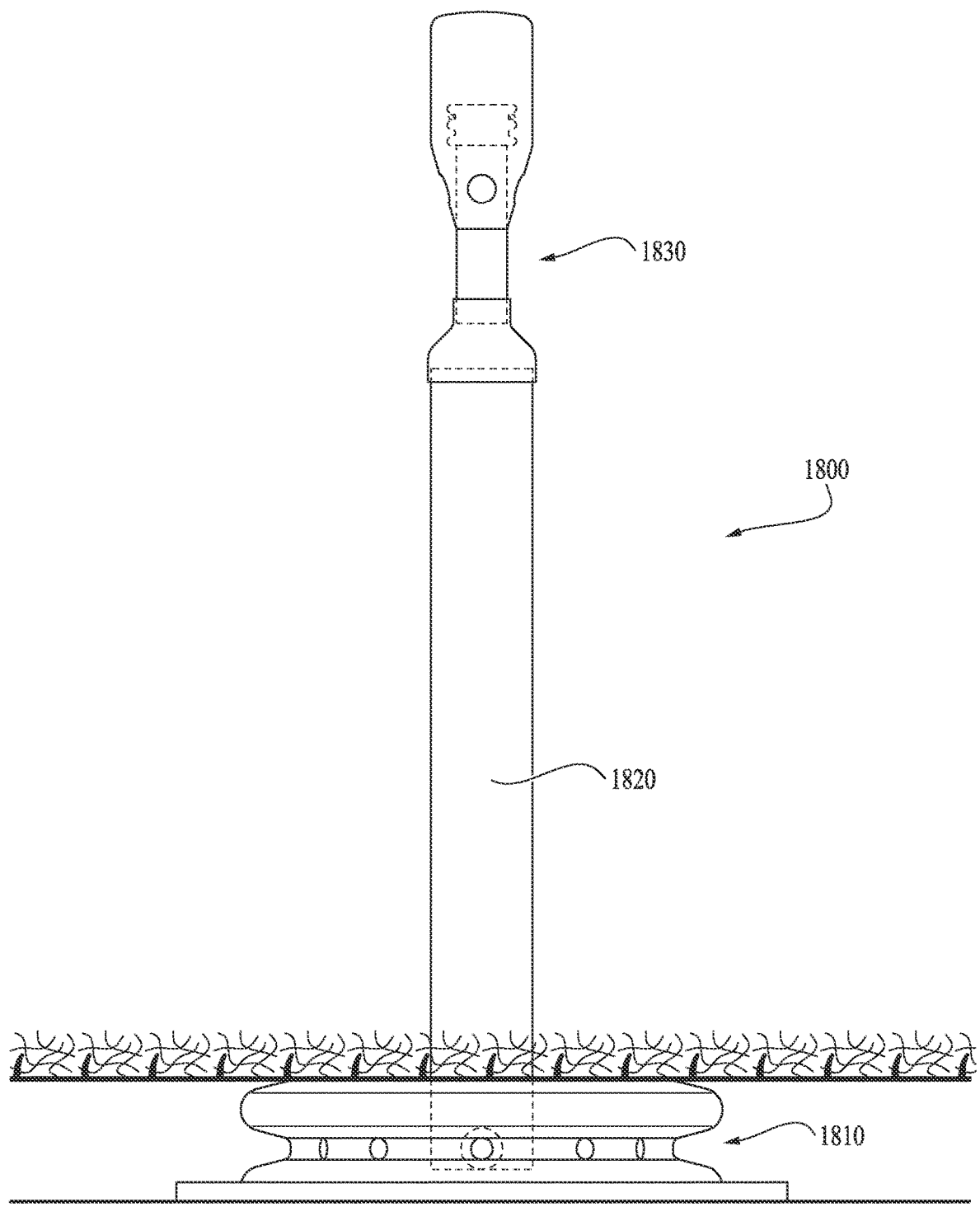
FIG. 18 is a schematic, sectional view of a shallow gas well of FIG. 14 in an example form of the present invention.

FIG. 18 shows a pressure relief valve 1800 of typical construction for use in the cover system 1400. Pressure relief valve 1800 includes a valve base 1810 positioned beneath the geomembrane and a valve stem 1820 connecting to the valve base 1820 and extending through the geomembrane. A Fernco fitting 1830 connects the valve stem to an upper portion of the valve including a valve body a valve sleeve and an exhaust port. Preferably, the valve material is polyethylene, stainless steel, neoprene, and Viton. Preferably, the pressure relief valve is designed for use in a vertical or near-vertical orientation. Preferably the pressure relief valve conveys a maximum design flow of about 50 SCFM at 1 inch of water column.

Figure 19:
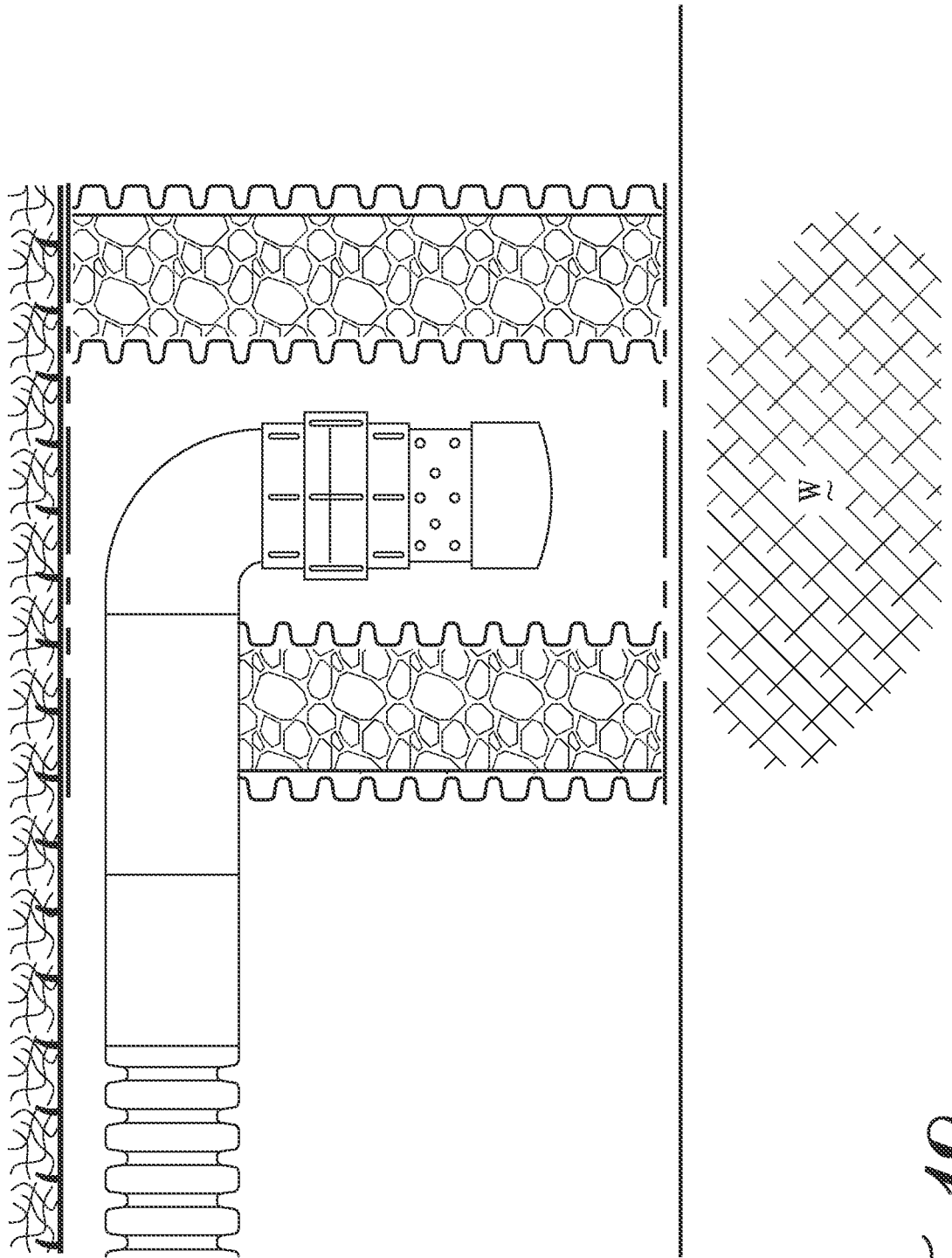
FIG. 19 is a schematic, sectional view of a shallow gas well of FIG. 14 in an example form of the present invention.

FIG. 19 shows a shallow gas collection well for use with the gas management cover system. The shallow gas collection well as shown in FIG. 19 is similar to collection wells depicted in prior figures of the present application.

Figure 20:
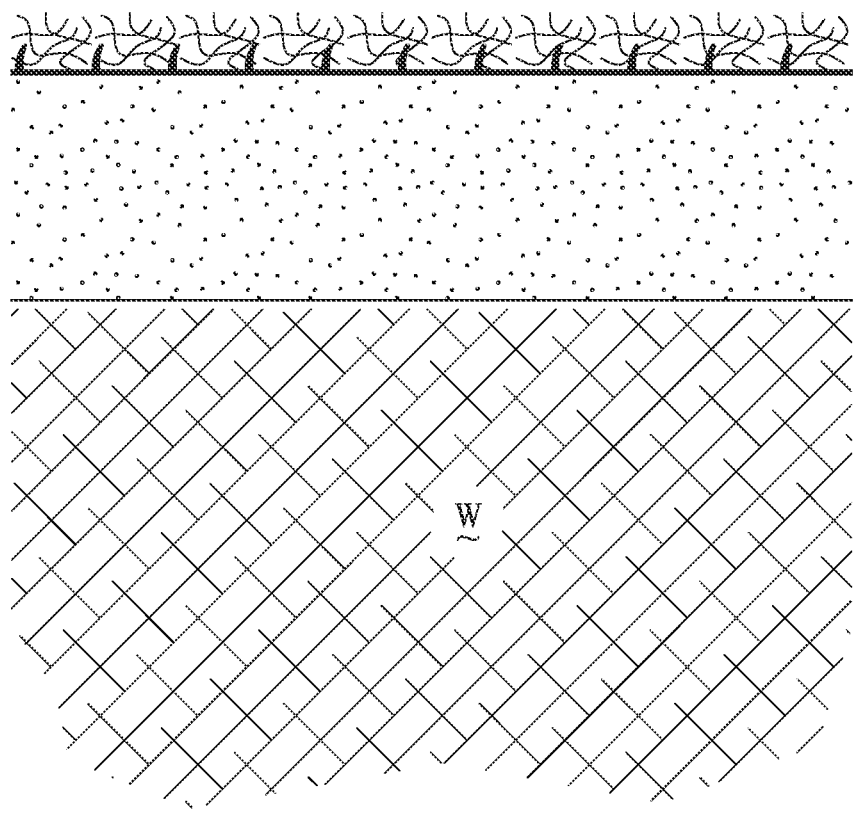
FIG. 20 is a schematic, sectional view of a cover and membrane portions of various forms of the present invention.

FIG. 20 shows a detailed view of protective cover positioned over a waste pile with a geomembrane and a woven or non-woven upper layer positioned atop the geomembrane and having a nominal thickness of about ¾ of an inch.

Figure 21:
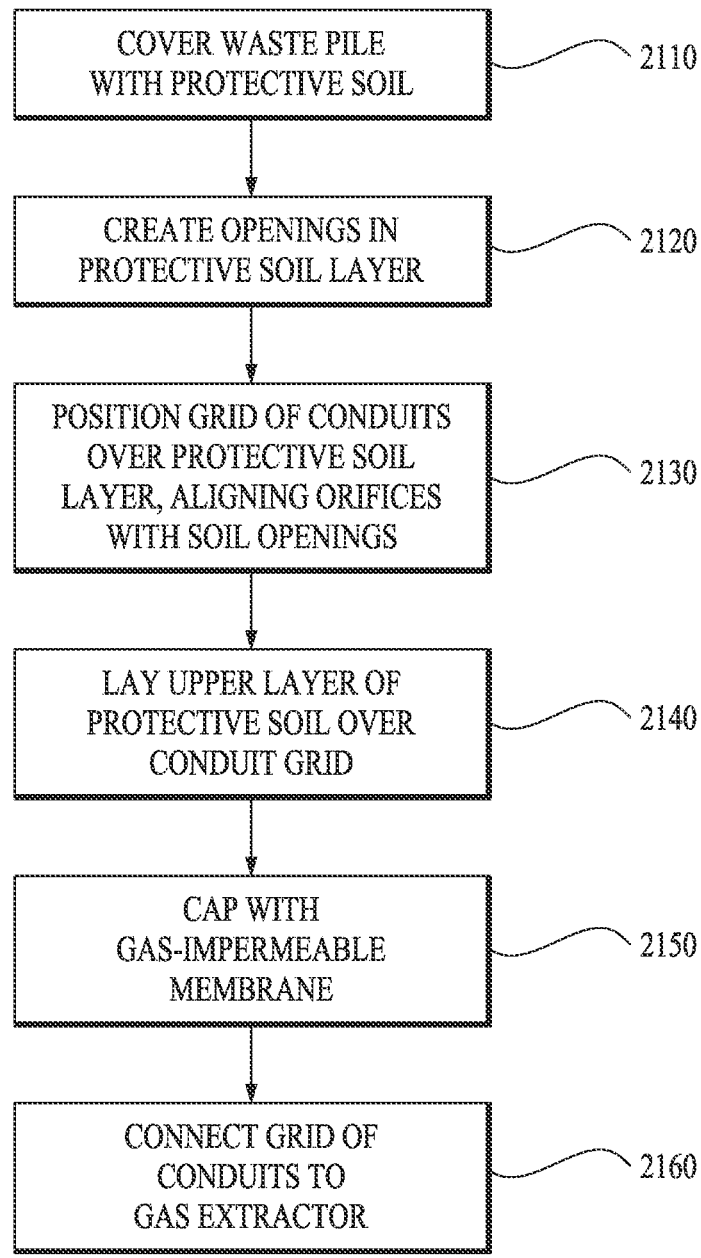
FIG. 21 is a schematic flow chart of a method for installing a collector grid for extracting and/or conveying sub-surface gas from a waste landfill according to another preferred example form of the present invention.

FIG. 21 shows, schematically, the method steps for installing a gas collector grid according to another example form of the present invention. As shown herein, at step 2110 one would cover the waste pile with protective soil. In the next step 2120, one would create openings in the protective soil layer. In a third step 2130, one would position a grid of conduits over the protective soil layer, while aligning the orifices with the openings in the soil. In the fourth step 2140, one would lay an upper layer of protective soil over the conduit grid. In a fifth step 2150, one would cap the site with a gas-impermeable membrane. And in a sixth step 2160, one would connect the grid of conduits to a gas extractor.

Figure 22A:
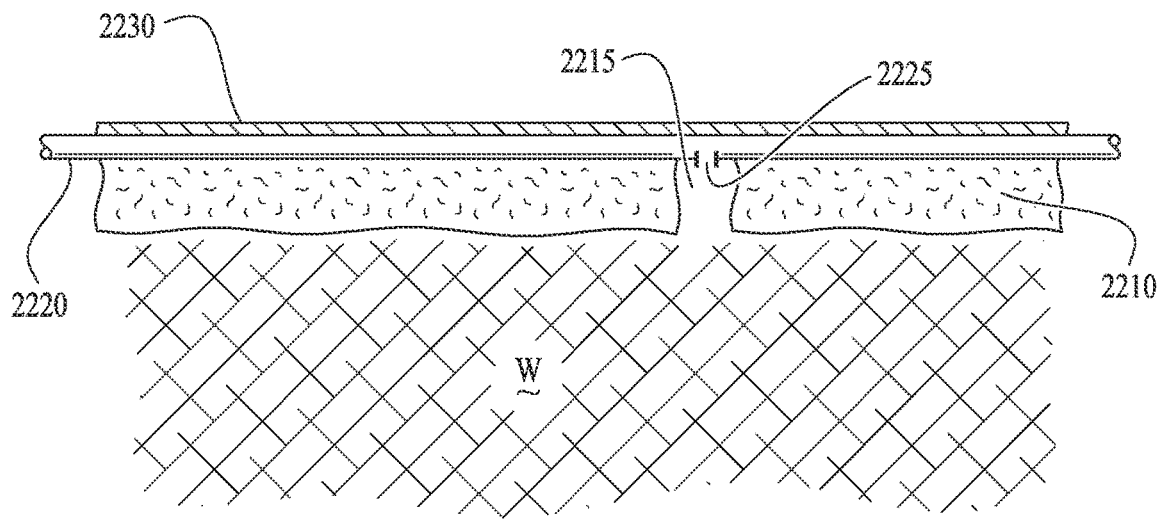
FIG. 22A is a schematic, sectional view of a collection grid in an example form of the present invention.

FIG. 22A depicts a collection grid in which a waste pile W is topped with a layer of soil 2210. The soil has openings 2215 created in it and a grid of conduits 2220 is positioned over the soil such that openings 2225 in the conduits are aligned with openings in the soil. A gas-impermeable membrane 2230 is positioned atop the conduit grid 2220.

Figure 22B:
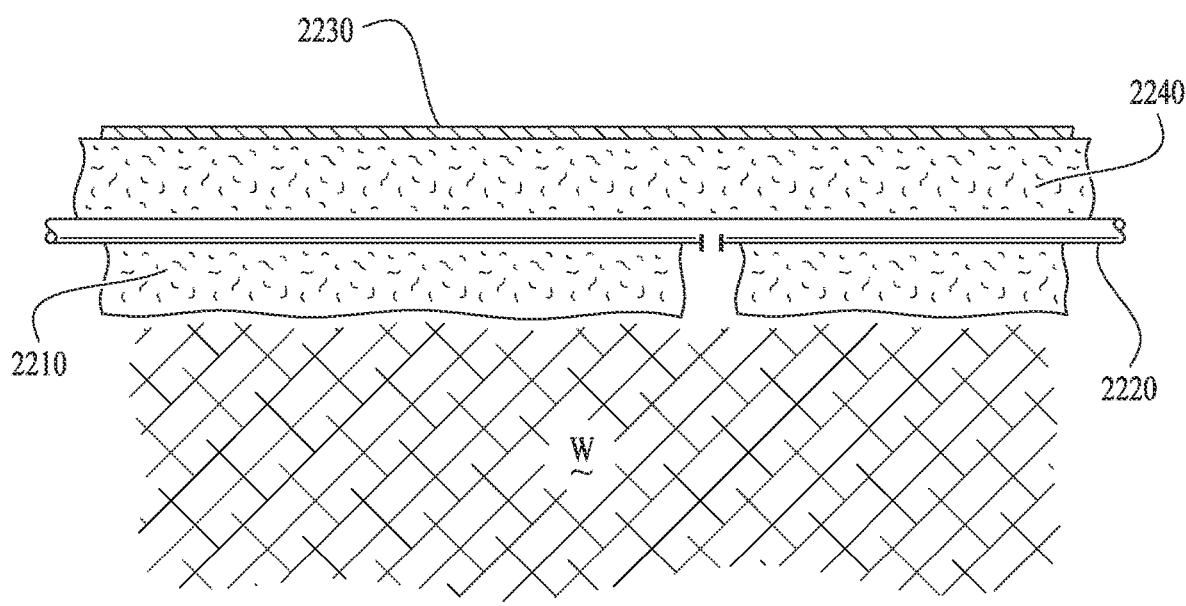
FIG. 22B is a schematic, sectional view of a collection grid in another example form of the present invention.

FIG. 22B shows a similar arrangement to the prior figure, with the notable difference being that an additional (upper) soil layer 2240 is positioned above the grid of conduits 2220 and then the membrane 2230 is positioned atop the upper soil layer 2240.

Figure 23:
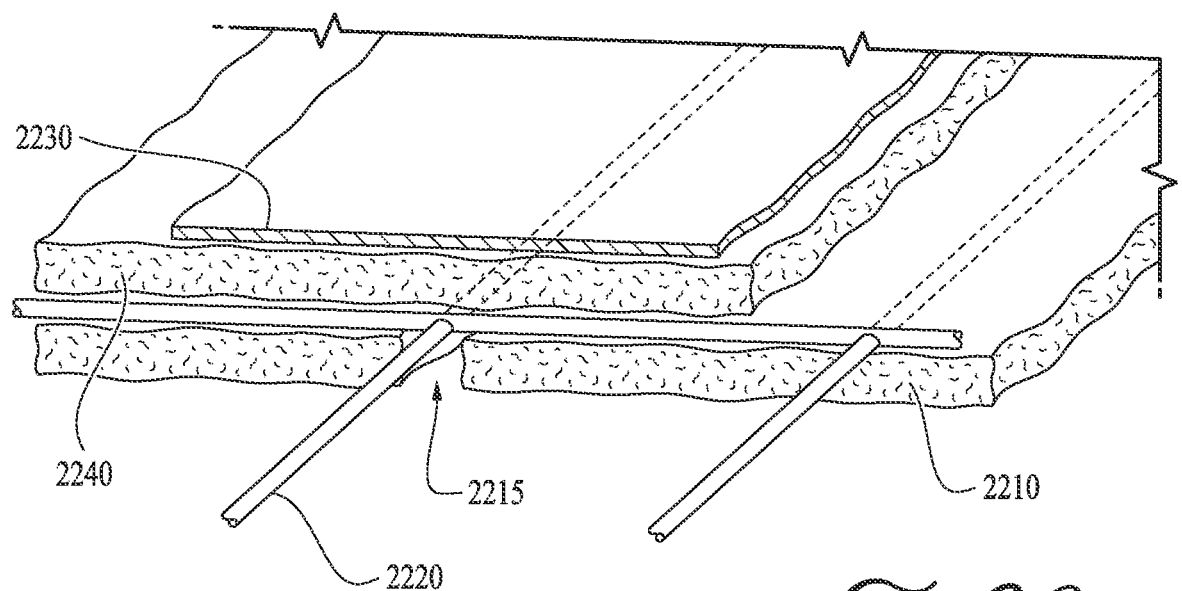
FIG. 23 is a schematic, perspective view of a portion of a collection grid in an example form of the present invention.
Figure 24:
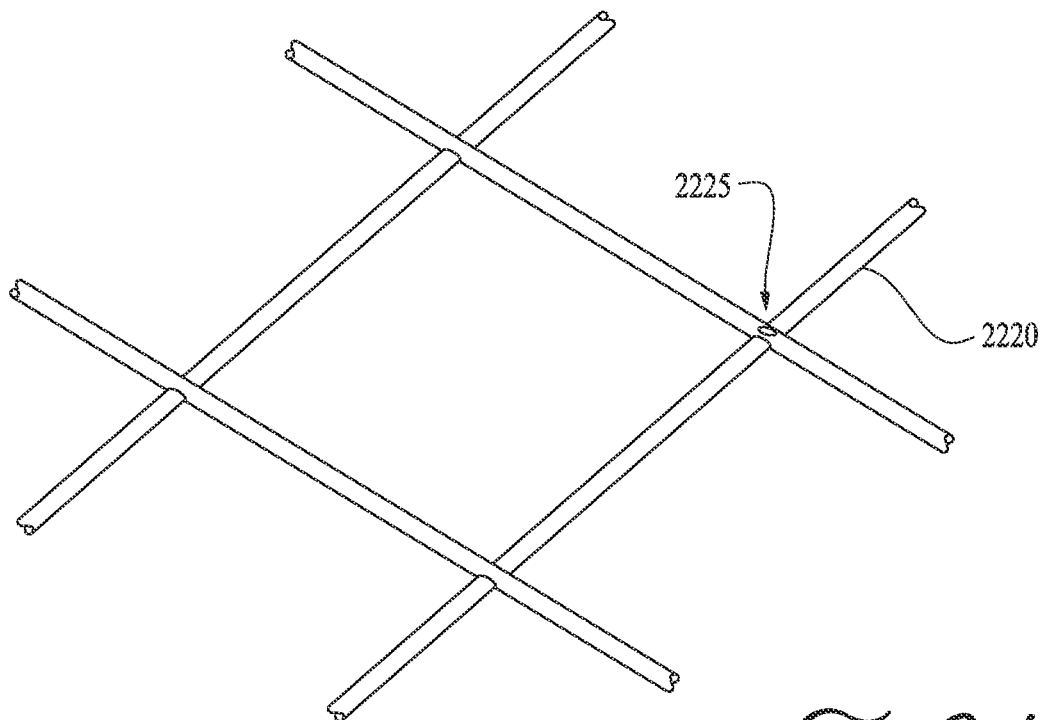
FIG. 24 is a schematic, perspective, partially-cutaway view of a collection grid in an example form of the present invention.
Figure 25A:
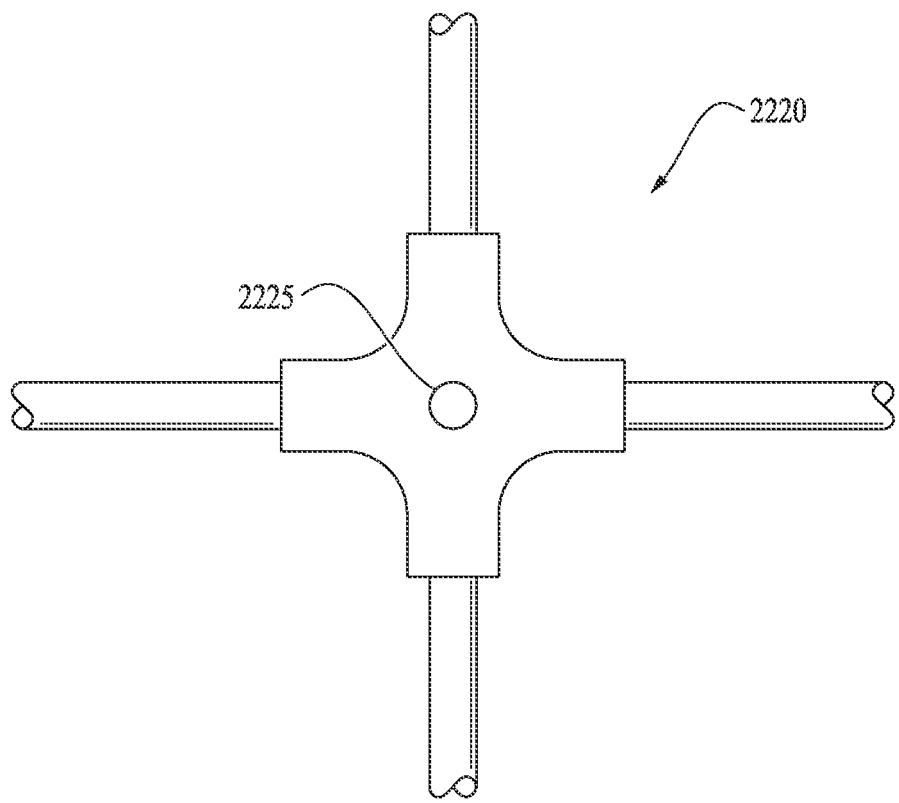
FIG. 25A is a schematic, plan view of a portion of a collection grid in an example form of the present invention.
Figure 25B:
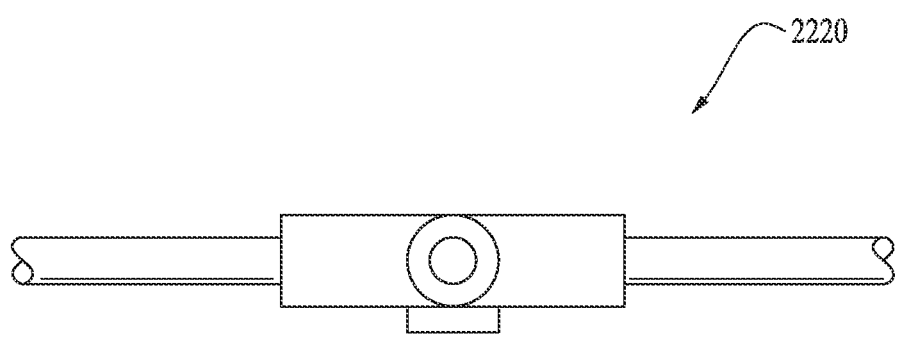
FIG. 25B is a schematic, side view of a portion of a collection grid in an example form of the present invention.

FIGS. 23-24 show the collection grid of FIGS. 22A and 22B in greater detail. FIGS. 25A and 25B are bottom and side views, respectively of the collector grid 2220 of FIGS. 22A and 22B.

By combining two or more of the following, outstanding results can be achieved in creating a strong, effective "zone of influence". One is to use a novel shallow gas collection well as described and shown herein. Another is to maintain available vacuum pressure across multiple gas collectors behind a single manual control valve. Preferably, one should utilize specific sized orifices and avoid manual control valves at the collection points. (The industry typically utilizes a manual control valve at each collector and cannot maintain a steady radius of influence throughout the collector's perforations.) Thirdly, one can avoid using a manual control valve or monitoring ports at the collection points. Fourthly, and importantly, one can avoid using membrane penetrations at the collection points. Known systems rely on penetrations to access each collection point for collector monitoring and well condensate removal. Fifth, an unlimited radius of influence (if radius of influence is defined as the area under the influence of negative pressure behind the manual control valve, then the novel system shown and described herein can be described as having a virtually unlimited radius of influence).

Advantageously, the above example forms of the present invention avoid perforations at the gas collection nodes/orifices. This eliminates a large number of perforations in the impermeable membrane, helping to maintain the structural integrity of the membrane and lengthening its effective service life.

It is to be understood that this invention is not limited to the specific devices, methods, conditions, or parameters described and/or shown herein, and that the terminology used herein is for the purpose of describing particular embodiments by way of example only. Thus, the terminology is intended to be broadly construed and is not intended to be limiting of the claimed invention. For example, as used in the specification including the appended claims, the singular forms "a," "an," and "one" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein.

While the invention has been shown and described in exemplary forms, it will be apparent to those skilled in the art that many modifications, additions, and deletions can be made therein without departing from the spirit and scope of the invention as defined by the following claims.

What is claimed is:

1. A gas collection system for use at landfills and the like of the type having a gas-producing waste pile, the gas collection grid comprising:
   a protective layer of soil positioned over the waste pile, with a grid pattern of vertical openings formed in the protective layer of soil and spaced apart from one another;
   an impermeable geomembrane; and
   a gas collector conduit grid extending laterally beneath the impermeable membrane and positioned within or atop the protective layer of soil and having a plurality of collection orifices formed adjacent the vertical openings formed in the protective layer of soil, and wherein the impermeable geomembrane is non-perforated adjacent the collection orifices and the gas collector conduit grid is adapted for delivering collected gas laterally from beneath the geomembrane rather than vertically through the geomembrane.

2. A gas collection system as claimed in claim 1 further comprising shallow gas wells positioned at spaced apart points on the grid, the shallow gas wells comprising:
   a non-perforated outer pipe extending generally toward the geomembrane;
   a perforated inner pipe positioned within and extending within the non-perforated outer pipe and together with the non-perforated outer pipe defining a space between the two pipes;
   a quantity of gravel-like material positioned within the space between the perforated inner pipe and the non-perforated outer pipe; and
   a transport conduit extending beneath the geomembrane and not extending through the membrane for transporting gas produced by the waste pile and collected through the gravel-like material and into and through the perforated inner pipe of the shallow gas well collector.

3. A gas collection system as claimed in claim 1 further comprising a lower geocomposite positioned over the gas-producing waste pile and an upper geocomposite positioned over the protective layer of soil such that the protective layer of soil is positioned between the lower and upper geocomposites.

4. A gas collection system as claimed in claim 1 further comprising an upper layer of soil positioned between the gas collector conduit grid and the impermeable membrane.

5. A gas collection system as claimed in claim 1 wherein the gas collector conduit grid is cruciform in general arrangement.

6. A gas collection system for use at landfills and the like of the type having a gas-producing waste pile, the gas collection grid comprising:
   a lower geocomposite positioned over the gas-producing waste pile;
   a protective layer of soil positioned over the lower geocomposite, with a grid pattern of vertical openings formed in the protective layer of soil spaced apart from one another;
   an upper geocomposite positioned over the protective layer of soil such that the protective layer of soil is positioned between the lower and upper geocomposites;
   an impermeable geomembrane positioned over the upper geocomposite; and
   a cruciform gas collector conduit grid extending laterally beneath the impermeable membrane and positioned within or atop the protective layer of soil and having a plurality of collection orifices formed adjacent the vertical openings formed in the protective layer of soil, and wherein the impermeable geomembrane is non-perforated adjacent the collection orifices and the cruciform gas collector conduit grid is adapted for delivering collected gas laterally from beneath the geomembrane rather than vertically through the geomembrane.

7. A collection grid as claimed in claim 1 wherein shallow gas wells are positioned at spaced apart points on the grid, the shallow gas wells comprising:
a non-perforated outer pipe extending generally from the lower geocomposite toward the upper geocomposite;
a perforated inner pipe positioned within and extending within the non-perforated outer pipe and together with the non-perforated outer pipe defining a space between the two pipes;
a quantity of gravel-like material positioned within the space between the perforated inner pipe and the non-perforated outer pipe; and
a transport conduit extending beneath the geomembrane and not extending through the membrane for transporting gas produced by the waste pile and collected through the gravel-like material and into and through the perforated inner pipe of the shallow gas well collector.

8. A method of installing a gas collection grid for use at landfills and the like of the type having a gas-producing waste pile, the method comprising the steps of:
covering the waste pile with a protective layer of soil;
creating vertical openings in the protective layer of soil spaced apart from one another in a grid pattern;
creating a cruciform grid of gas collector conduits having a series of gas collection orifices space apart from one another to generally match the spacing of the grid pattern of vertical openings in the protective soil layer and positioning the grid of gas collector conduits such that the orifices generally are aligned with the vertical openings in the protective soil layer;
covering the grid of gas collector conduits with an upper layer of soil;
placing a gas-impermeable membrane over the upper layer of soil; and
connecting the grid of gas collector conduits with an external gas extraction apparatus.

\* \* \* \* \*